United States Patent [19]

Kato et al.

[11] Patent Number: 5,789,436
[45] Date of Patent: Aug. 4, 1998

[54] 4,6 DI-T-BUTYL-5-HYDROXY-2,3-DIHYDROBENZOTHIOPHENE

[75] Inventors: Yoshiaki Kato; Akira Ishikawa; Kunio Tamura, all of Shizuoka-ken, Japan

[73] Assignee: Chugai Seiyak Kabushiki Kaisha, Tokyo, Japan

[21] Appl. No.: 727,652

[22] PCT Filed: Apr. 11, 1995

[86] PCT No.: PCT/JP95/00706

§ 371 Date: Oct. 9, 1996

§ 102(e) Date: Oct. 9, 1996

[87] PCT Pub. No.: WO95/27710

PCT Pub. Date: Oct. 19, 1995

[30] Foreign Application Priority Data

Apr. 11, 1994 [JP] Japan .................. 6-107365

[51] Int. Cl.[6] .............. A61K 31/38; C07D 333/52; C07D 333/64; C07C 321/00
[52] U.S. Cl. .............. 514/443; 549/51; 549/52; 549/53; 549/54; 549/59; 549/60; 564/162
[58] Field of Search .............. 549/51, 52, 53, 549/54, 59, 60; 514/443; 564/162

[56] References Cited

U.S. PATENT DOCUMENTS

| 3,530,146 | 9/1970 | Newman et al. | 549/51 |
|---|---|---|---|
| 4,001,426 | 1/1977 | Brenner et al. | 549/57 |
| 4,224,330 | 9/1980 | Henrick et al. | 549/51 |
| 4,362,740 | 12/1982 | Inada et al. | 549/52 |
| 4,418,068 | 11/1983 | Jones | 549/51 |
| 4,436,748 | 3/1984 | Ong et al. | 549/53 |
| 4,654,352 | 3/1987 | Ray | 514/443 |
| 4,665,206 | 5/1987 | Redpath et al. | 549/51 |
| 4,963,580 | 10/1990 | Zambias et al. | 514/443 |
| 5,112,852 | 5/1992 | McCarthy et al | 514/443 |
| 5,147,889 | 9/1992 | Ferrini | 514/443 |
| 5,244,893 | 9/1993 | Elbe et al. | 514/443 |
| 5,292,894 | 3/1994 | Ebel et al. | 549/51 |

FOREIGN PATENT DOCUMENTS

| 0140297 | 5/1985 | European Pat. Off. . |
|---|---|---|
| 0639573 | 2/1995 | European Pat. Off. . |
| 005356 | 1/1975 | Japan . |
| 2224028 | 4/1990 | United Kingdom . |

OTHER PUBLICATIONS

R. Robillard et al., "Total Synthesis of 1-Thio-α-Tocopherol: A Sulfur-Containing Analogue of Vitamin E[1]", Tetrahedron Letters, vol. 27, No. 25, pp. 2817-2810m 1986.

R. Robillard et al., "Synthesis of 2-Substituted 5,7,8-Trimethyl-6-Hydroxythiochromans and Purported Syntheses of Sulfur-Containing Analogues of Vitamin E[1]", J. Org. Chem., vol. 51, pp. 1700-1704, 1986.

H.A. Zahalka et al., "Antioxidant Activity of 1-Thio-α-Tocopherol and Related Compounds. EPR, Endor and UV-Visible Absorption Spectra of Some of the Derived Phenoxyl Radicals[1]", J. Org. Chem., vol. 53, pp. 3739-3745 1988.

R.A. Zambias et al., "The Synthesis of 5-Hydroxy-2,3-Dihydrobenzo(B)Thiophene (1) Via an Efficient One Step Preparation of 5-Nitro-Benzo(B)Thiophene-2-Carboxylate (3a)", Synthetic Communications, vol. 21, No. 7, pp. 959-964, 1991.

M.S. Newman et al., "The Conversion of Phenols to Thiophenols via Dialkylthiocarbamates1", J. Org. Chem., vol. 31, pp. 3980-3984, 1966.

L.K.A. Rahman et al., "7-Substituted Benzo|b|Thiophenes and 1,2-Benzisothiazoles. Part 1. Hydroxy- or Methoxy-Derivatives", J. Chem. Soc. Perkin Trans. I, pp. 2973-2977, 1983.

P. Karrer et al., "Über Einige Thiochromanderivate Mit Tocopherol-Struktur", Helv. Chim. Acta, vol. 27, pp. 678-684, 1944.

Wagner et al., "Hypolipidemic Arylthioalkanoic Acids", Journal of Mediincal Chemistry, vol. 20, No. 8, pp. 1007-1013, Mar. 4, 1977.

Fujisawa, "Thiocarbamic Acid Esters Having Hindered Phenol Groups", Chemical Abstracts, vol. 82, No. 21, p. 595, May 26, 1975.

Primary Examiner—Deborah C. Lambkin
Attorney, Agent, or Firm—Browdy and Neimark

[57] ABSTRACT

A compound represented by formula (I):

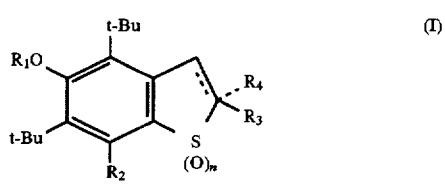

wherein $R_1$ represents a hydrogen atom, a lower alkyl group or an acyl group; $R_2$ and $R_3$, which may be the same or different, each represents a hydrogen atom, an optionally substituted alkyl group, or an optionally substituted alkenyl group; $R_4$ represents a hydrogen atom, an optionally substituted alkyl group, or an optionally substituted alkenyl group, or $R_4$ forms a double bond between the carbon atom to which $R_3$ is bonded and the adjacent carbon atom to form a benzothiophene skeleton, or $R_3$ and $R_4$ are taken together to form a 5- to 8-membered spiro ring which may contain a hetero atom, e.g., oxygen, sulfur or nitrogen; and n represents an integer of 0 to 2, or a pharmaceutically acceptable salt thereof. The compound of formula (I) exhibits an inhibitory action on the oxidative modification of LDL and is useful as therapeutics of arteriosclerosis.

14 Claims, No Drawings

4,6 DI-T-BUTYL-5-HYDROXY-2,3-DIHYDROBENZOTHIOPHENE

This application is a 371 of PCT/JP95/00706 filed Apr. 11, 1995.

1. Technical Field

This invention relates to compounds which prevent the oxidative modification of LDL, more particularly, to compounds useful as therapeutics of arteriosclerosis, myocardial infarction, etc.

2. Background Art

Atherosclerosis is one of the principal causes of ischemic diseases such as angina pectoris, myocardial infarction and cerebral apoplexy. The mechanism of initiation and progression of atherosclerosis is closely related to the oxidative modification of LDL. The modified LDLs are not recognized by the LDL receptor but by the scavenger receptor, to induce the foam cell formation which is characterized by cholesterol accumulation.

The modification of LDL is caused by endothelial cells, smooth muscle cells, macrophages, etc. and the modified LDLs are eventually taken by macrophages via the scavenger or other pathways. It is additionally known that the modification of LDL by these cells is similar to the oxidative modification of LDL by $Cu^{2+}$.

LDL is chiefly composed of cholesterol esters, phospholipids and apo-B-100. The oxidative modification of LDL is shown from various aspects, for example fragmentation of apo-B-100 by the generated radicals, the reaction between the lipid peroxidation products and the free amino groups in apo-B-100 lysine residues, and the transformation of phosphatidyl choline to a lyso-form. One of the most established phenomena in LDL oxidation is an increase of thiobarbituric acid reactive substances (TBARS) as a result of the lipid peroxidation. Oxidized LDL, or LDL that has undergone such oxidative modification, causes the foam cell formation and the cholesterol accumulation by the scavenger and other pathways.

Under these circumstances, it is expected that compounds having the inhibitory action on lipid peroxidation can inhibit the initiation and progression of atherogenic lesions by preventing the oxidative modification of LDL and, hence, have the potential to work as therapeutics of arteriosclerosis.

In ischemic diseases such as cerebral apoplexy and myocardial infarction, various active oxygen species are generated during blood reperfusion at ischemic sites and tissue disorders can be exacerbated by the disruption of cell membranes and other effects caused by the lipid peroxidation. It is expected that compounds having the anti-oxidative activity can prevent the tissue disorders in ischemic lesions by removing the various active oxygen species and lipid peroxidation and, hence, have the potential to work as therapeutics of ischemic diseases.

Vitamin E is known as a natural antioxidant and studies have been made to develop synthetic antioxidants using vitamin E as the basic skeleton but no completely satisfactory products have yet been synthesized.

Some of the compounds of the present invention which are represented by formula (I) shown below are described, by their generic concept, in British Patent Publication GB 2224028, but the publication has no mention of antioxidant activity and applicability as therapeutics of arteriosclerosis.

DISCLOSURE OF THE INVENTION

An object of the present invention is to provide antioxidants useful for the treatment of arteriosclerosis and other ischemic diseases such as myocardial infarction and cerebral apoplexy, as well as intermediates useful for preparing said compounds.

The inventors of the present invention thought that the reason for the insufficient efficacy of conventional antioxidants, such as the compounds disclosed in Japanese Patent Publication Laid-Open No. 121975/90, is that their activity is lost before they reach the target site. Because they easily react with various free radical species besides lipid peroxidation related radicals. Based on this assumption, the inventors have conducted extensive investigations for the purpose of developing efficient antioxidants having higher reaction specificity. It has been found as a result that the above object is accomplished by the compounds represented by formula (I):

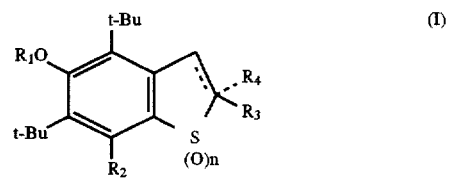

wherein $R_1$ represents a hydrogen atom, a lower alkyl group or an acyl group; $R_2$ and $R_3$, which may be the same or different, each represents a hydrogen atom, an optionally substituted alkyl group, or an optionally substituted alkenyl group; $R_4$ represents a hydrogen atom, an optionally substituted alkyl group, or an optionally substituted alkenyl group, or $R_4$ forms a double bond between the carbon atom to which $R_3$ is bonded and the adjacent carbon atom to form a benzothiophene skeleton, or $R_3$ and $R_4$ are taken together to form a 5- to 8-membered spiro ring which may contain a hetero atom, e.g., oxygen, sulfur or nitrogen; and n represents an integer of 0 to 2.

It has also been found that compounds represented by formula (II):

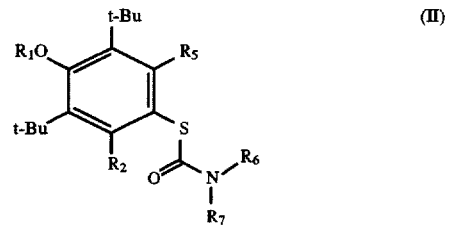

wherein $R_1$ and $R_2$ are as defined above; $R_5$ represents a group of formula (III):

wherein $R_8$ and $R_9$, which may be the same or different, each represents a hydrogen atom, an optionally substituted alkyl group or an optionally substituted alkenyl group, a group of formula (IV):

wherein $R_8$, $R_9$, and $R_{10}$, which may be the same or different, each represents a hydrogen atom, an optionally substituted alkyl group or an optionally substituted alkenyl group, or a group of formula (V):

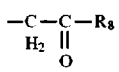

(V)

wherein $R_8$ is as defined above; and $R_6$ and $R_7$, which may be the same or different, each represents a lower alkyl group, are novel compounds that have not been reported in the literature and intermediates useful for synthesizing the compounds represented by formula (I).

It should be mentioned that the compounds of the invention which are represented by the general formula (I) have the following three characteristic features:

(1) They are lipid-soluble antioxidants which inhibit lipid peroxidation efficiently;

(2) While there are many species of free radicals that are involved in oxidation, the compounds react efficiently with those radical species which are responsible for the chain reaction of lipid peroxidation, therefore they inhibit lipid peroxidation intensely.

(3) In order to develop the specific lipid peroxidation inhibiting action to be specific in lipids, the compounds have low reactivity for so-called "active oxygen" species (e.g. superoxides and singlet oxygen) in aqueous solution.

THE BEST MODE FOR CARRYING OUT THE INVENTION

The compounds represented by formula (I) are novel compounds having two t-butyl groups on both ortho-positions of the phenolic hydroxyl group, not being found in the literature. British Patent Publication GB 224028 discloses the generic concept including some of the compounds of the present invention, but no specific mention of the compounds is given.

The present invention is based on the fact that the compounds represented by formula (I) having two t-butyl groups on both ortho-positions of the phenolic hydroxyl group exert markedly excellent effects as demonstrated in Test Examples hereinafter given. The present invention provides the compounds represented by formula (I) and pharmaceutically acceptable salts thereof. The invention also includes optically active isomers of the compounds.

In the formulae used herein, the term "lower alkyl group" is intended to mean a straight-chain or branched alkyl group having 1 to 6 carbon atoms and includes methyl, ethyl, n-propyl, isopropyl, n-butyl, s-butyl, and t-butyl groups. The acyl group includes acetyl, formyl, propionyl, benzoyl, and benzyloxycarbonyl group, with an acetyl group being preferred.

The term "optionally substituted alkyl group" is intended to mean a straight-chain or branched optionally substituted alkyl group having 1 to 20 carbon atoms, such as methyl, ethyl, n-propyl, isopropyl, n-butyl, sec-butyl, t-butyl, pentyl, hexyl, heptyl, octyl, nonyl and decyl groups.

The term "optionally substituted alkenyl group" means a straight-chain or branched optionally substituted alkenyl group having 2 to 20 carbon atoms, such as vinyl, allyl, butenyl, pentenyl, geranyl and farnesyl groups.

The substituent of the substituted alkyl or alkenyl group includes a halogen atom, a hydroxyl group, an amino group which may be substituted with a straight-chain or branched alkyl group having 1 to 6 carbon atoms, an alkoxy group, and an aryloxy group.

Specific examples of the compound of formula (I) according to the invention are shown below.

4,6-Di-t-butyl-5-hydroxy-2,2-di-n-pentyl-2,3-dihydrobenzothiophene, 4,6-Di-t-butyl-5-hydroxy-2-methyl-2,3-dihydrobenzothiophene, 4,6-Di-t-butyl-5-hydroxy-2,2-dimethyl-2,3-dihydrobenzothiophene, 4,6-Di-t-butyl-5-hydroxybenzo[b]thiophene, 4,6-Di-t-butyl-5-hydroxy-2,3-dihydrobenzothiophene, 4,6-Di-t-butyl-5-hydroxy-2,2-diethyl-2,3-dihydrobenzothiophene, 4,6-Di-t-butyl-5-hydroxy-2,2-di-n-propyl-2,3-dihydrobenzothiophene, 4,6-Di-t-butyl-5-hydroxy-2,2-diisopropyl-2,3-dihydrobenzothiophene, 4,6-Di-t-butyl-5-hydroxy-2,2-di-n-butyl-2,3-dihydrobenzothiophene, 4,6-Di-t-butyl-5-hydroxy-2,2-diisoamyl-2,3-dihydrobenzothiophene, 4,6-Di-t-butyl-5-hydroxy-2,2-di-n-hexyl-2,3-dihydrobenzothiophene, 4,6-Di-t-butyl-5-hydroxy-2,2-di-n-heptyl-2,3-dihydrobenzothiophene, 4,6-Di-t-butyl-5-hydroxy-2,2-di-n-octyl-2,3-dihydrobenzothiophene, 4,6-Di-t-butyl-5-hydroxy-2,2-diphenyl-2,3-dihydrobenzothiophene, 4,6-Di-t-butyl-5-hydroxy-2,2-dibenzyl-2,3-dihydrobenzothiophene, 4,6-Di-t-butyl-5-hydroxy-2-methyl-2-(4,8,12-trimethyltrideca-3(E),7(E),11-trienyl)-2,3-dihydrobenzothiophene, 4,6-Di-t-butyl-5-hydroxy-2-methyl-2-(4,8,12-trimethyltridecyl)-2,3-dihydrobenzothiophene, 4,6-Di-t-butyl-5-hydroxy-2-n-octyl-2,3-dihydrobenzothiophene, 2,4,6-Tri-t-butyl-5-hydroxy-2,3-dihydrobenzothiophene, 4,6-Di-t-butyl-5-hydroxy-2,2-dimethyl-7-n-propyl-2,3-dihydrobenzothiophene, 4,6-Di-t-butyl-5-hydroxy-2,3-dihydrobenozothiophene-2-spiro-1'-cyclopentane, 4,6-Di-t-butyl-5-hydroxy-2,3-dihydrobenzothiophene-2-spiro-1'-cyclohexane, 4,6-Di-t-butyl-5-hydroxy-2,3-dihydrobenzothiophene-2-spiro-1'-cycloheptane, 4,6-Di-t-butyl-5-hydroxy-2,3-dihydrobenzothiophene-2-spiro-1'-cyclooctane, 4,6-Di-t-butyl-2-methyl-5-hydroxybenzo[b]thiophene, 2,4,6-Tri-t-butyl-5-hydroxybenzo[b]thiophene, 4,6-Di-t-butyl-2-octyl-5-hydroxybenzo[b]thiophene, 4,6-Di-t-butyl-5-hydroxy-2-(N,N-dimethylaminomethyl)-2-methyl-2,3-dihydrobenzothiophene, 4,6-Di-t-butyl-5-hydroxy-2-hydroxymethyl-2-methyl-2,3-dihydrobenzothiophene, 4,6-Di-t-butyl-5-hydroxy-2-methyl-2-(4,8-dimethylnona-3(E),7-dienyl)-2,3-dihydrobenzothiophene, and 4,6-Di-t-butyl-5-hydroxy-2-methyl-2-(4,8-dimethylnonyl)-2,3-dihydrobenzothiophene.

The compounds according to the invention can be synthesized, for example, as follows.

Method A

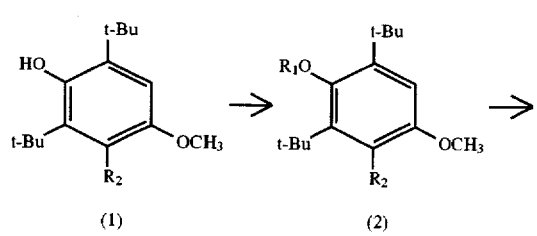

(1) → (2)

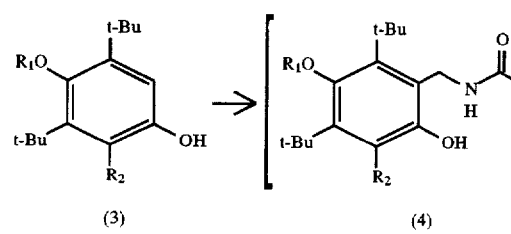

(3) → (4)

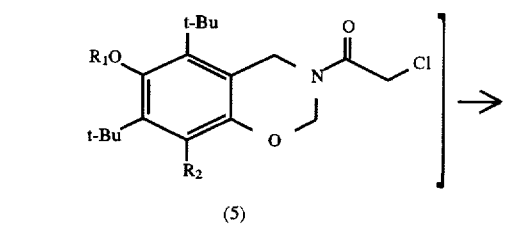

(5)

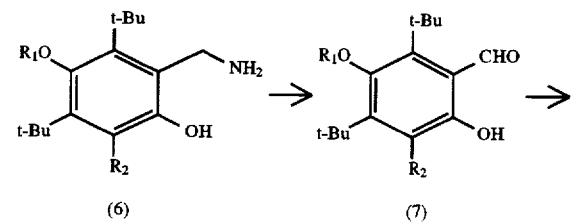

(6) → (7)

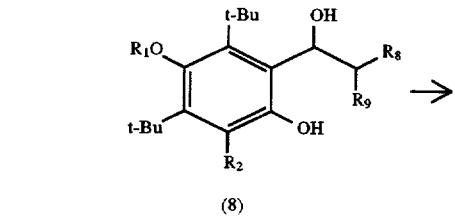

(8)

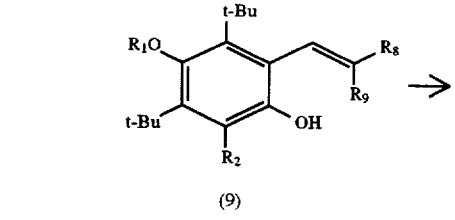

(9)

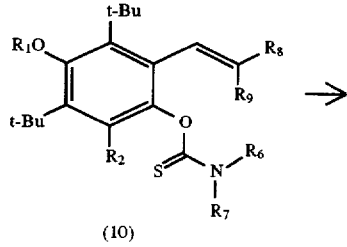

(10)

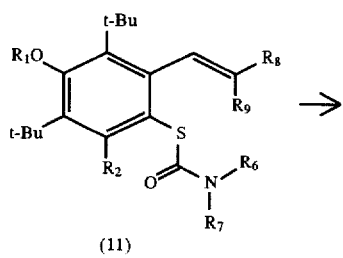

(11)

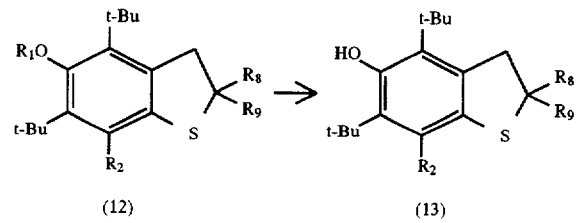

(12) → (13)

wherein $R_1$ represents a hydrogen atom, a lower alkyl group or an acyl group; $R_2$ represents a hydrogen atom, an optionally substituted alkyl group, or an optionally substituted alkenyl group; $R_6$ and $R_7$, which may be the same or different, each represents a lower alkyl group; and $R_8$ and $R_9$, which may be the same or different, each represents a hydrogen atom, an optionally substituted alkyl group, or an optionally substituted alkenyl group; or $R_8$ and $R_9$ are taken together to form a 5- to 8-membered spiro ring which may contain a hetero atom, such as an oxygen atom, a sulfur atom or a nitrogen atom.

Method B

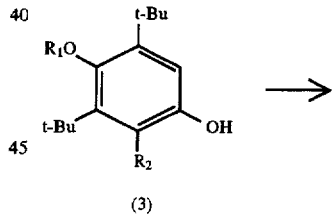

(3)

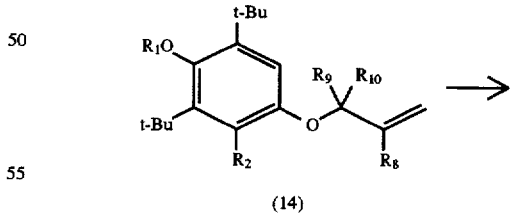

(14)

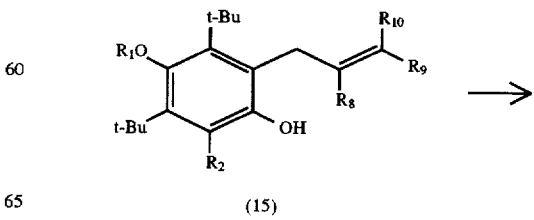

(15)

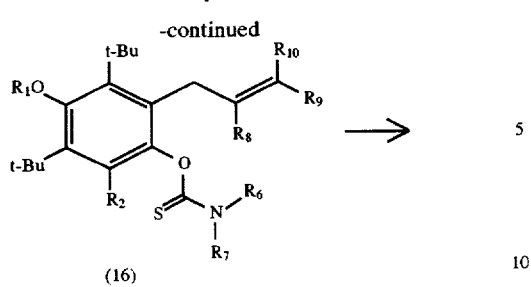
(16)
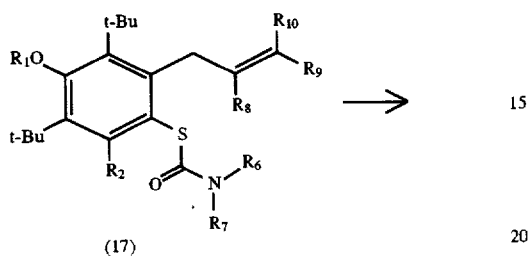
(17)
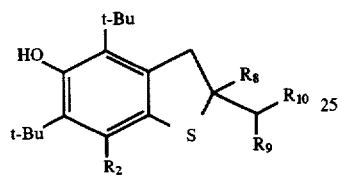
(18)
wherein $R_1$, $R_2$, $R_6$, and $R_7$ are as defined above; $R_8$, $R_9$, and $R_{10}$, which may be the same or different, each represents a hydrogen atom, an optionally substituted alkyl group, or an optionally substituted alkenyl group.
Method C
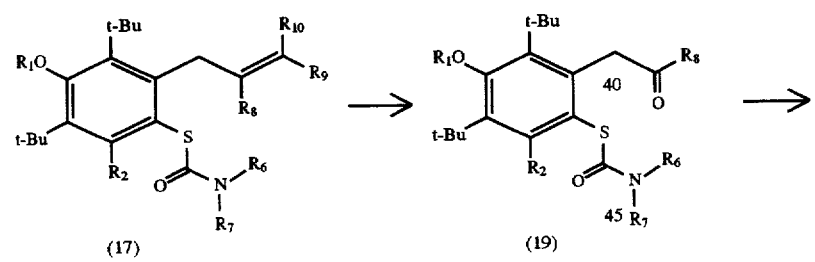
(17)     (19)
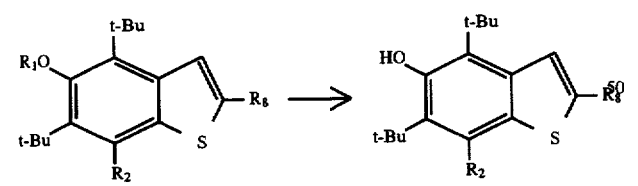
(20)     (21)
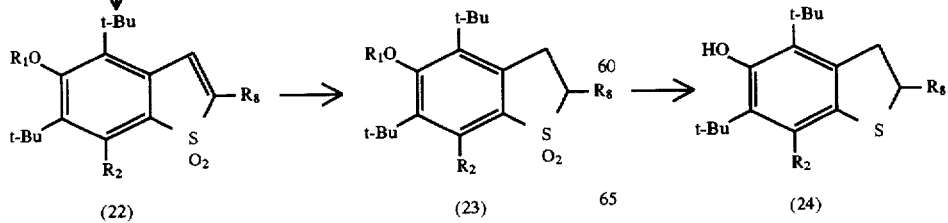
(22)     (23)     (24)

wherein $R_1$, $R_2$, $R_6$, $R_7$, $R_8$, $R_9$, and $R_{10}$ are as defined above.
Method D

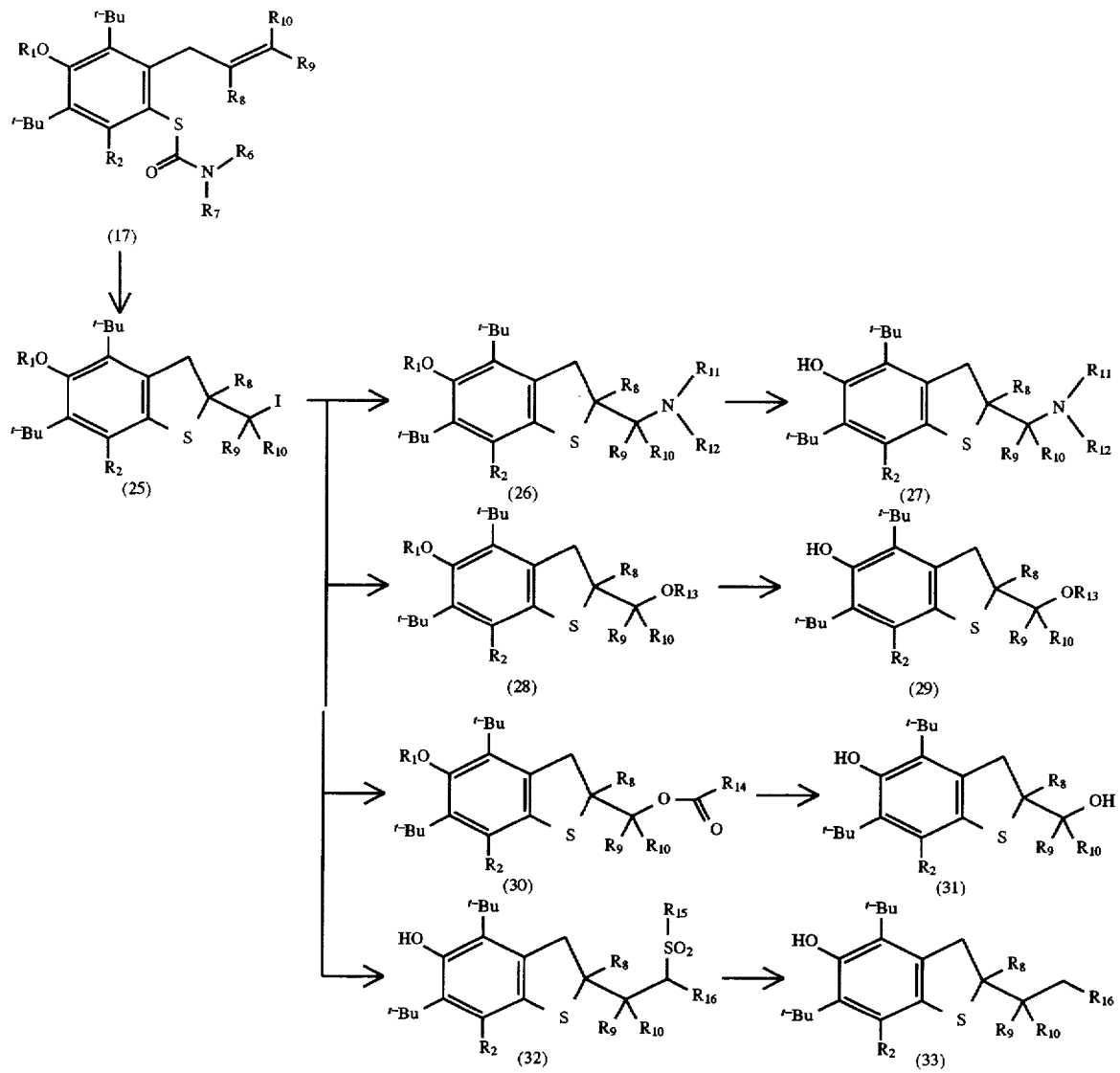

wherein $R_1$, $R_2$, $R_6$, $R_7$, $R_8$, $R_9$, and $R_{10}$ are as defined above; $R_{11}$ and $R_{12}$, which may be the same or different, each represents a straight-chain or branched alkyl group having 1 to 6 carbon atoms; $R_{13}$ represents a straight-chain or branched alkyl group having 1 to 20 carbon atoms; $R_{14}$ represents a lower alkyl group; $R_{15}$ represents a phenyl group which may be substituted with a lower alkyl group; and $R_{16}$ represents a hydrogen atom, an optionally substituted alkyl group, or an optionally substituted alkenyl group.

In method A, the phenolic hydroxyl group of compound (1) is protected to give compound (2). Compound (2) is demethylated by reaction with, e.g., iodotrimethylsilane to obtain compound (3). Compound (3) is reacted with N-hydroxymethyl-2-chloroacetamide in an acetic acid/sulfuric acid mixture at room temperature to obtain a mixture of compound (4) and compound (5). The mixture of compound (4) and compound (5) is heated under reflux in an ethanol/concentrated hydrochloric acid mixture to form compound (6). Compound (6) is dissolved in an acid aqueous solution, and hexamethylenetetramine is added to the solution, followed by heating to obtain compound (7). This reaction is preferably carried out by dissolving compound (6) in an acetic acid aqueous solution, adding hexamethylenetetramine, heating under reflux, and adding thereto a hydrochloric acid aqueous solution, followed by heating under reflux. Compound (7) is subjected to Grignard reaction to obtain compound (8). Compound (9) is obtained from compound (8) by dehydration reaction, for example, reaction with thionyl chloride in pyridine at room temperature. Compound (9) is thiocarbamoylated with N,N-dialkylthiocarbamoyl chloride to give compound (10). Compound (10) is heated under reflux in a solvent, e.g., diphenyl ether, to give compound (11). Compound (11) is reacted with a Lewis acid, e.g., boron trifluoride etherate in a solvent, e.g., chloroform, dichloromethane or diethyl ether, at room temperature to afford compound (12). The protective group of compound (12) is removed to yield compound (13).

In method B, compound (3) is reacted with an alkenyl halide, such as 3-chloro-2-methyl-1-propene, in a solvent, e.g., tetrahydrofuran, N,N-dimethylformamide, N,N- dimethylacetamide or acetone, in the presence of a base, e.g., sodium hydride, potassium carbonate, sodium carbonate, sodium hydroxide or potassium hydroxide, to obtain compound (14), which is then subjected to rearrangement by heating in a solvent, e.g., N,N-dimethylaniline or N,N-diethylaniline, to give compound (15). Compound (15) is thiocarbamoylated with an N,N-dialkylthiocarbamoyl chloride to give compound (16). Compound (16) is heated under reflux in a solvent, e.g., diphenyl ether to afford compound (17). Compound (17) is subjected to protective group removal and cyclization simultaneously to obtain compound (18).

In method C, compound (17) obtained in method B is reacted with sodium periodate etc. in the presence of a catalytic amount of osmium tetroxide in a mixed solvent of water and tetrahydrofuran, dioxane, methanol, ethanol etc. at room temperature to give compound (19). Compound (19) is cyclized by heating under reflux in a solvent, e.g., benzene or toluene, in the presence of a catalytic amount of p-toluenesulfonic acid, or in a solvent, e.g., chloroform, dichloromethane or diethyl ether, in the presence of a Lewis acid, e.g., boron trifluoride etherate, to give compound (20). Removal of the protective group of compound (20) affords compound (21). Separately, compound (20) is oxidized by reacting with, e.g., hydrogen peroxide, in a solvent, such as acetic acid, to give compound (22), which is then catalytically reduced in a solvent, e.g., ethyl acetate, methanol or ethanol, in the presence of palladium-on-carbon or a like catalyst to give compound (23). Compound (23) is reacted with, for example, lithium aluminum hydride in a solvent, e.g., tetrahydrofuran, to remove the protective group and conduct reduction simultaneously to yield compound (24).

In method D, compound (25) is derived from compound (17) obtained in method B by reacting compound (17) with iodine in a mixed solvent of water and diethyl ether, etc. in the presence of a base, e.g., sodium hydrogencarbonate, at room temperature. From compound (25) are obtained various derivatives according to the following four routes.

1. Compound (25) is reacted with ammonia or an alkylamine (a primary amine, a secondary amine, etc.) in a solvent, e.g., N,N-dimethylformamide, in the presence of a base, e.g., potassium carbonate, to obtain compound (26). Removal of the protective group of compound (26) gives compound (27).
2. Compound (25) is reacted with an alkyl alcohol, etc. in a solvent, e.g., N,N-dimethylformamide, in the presence of a base, e.g., sodium hydride, to obtain compound (28). Removal of the protective group of compound (28) yields compound (29).
3. Compound (25) is reacted with a carboxylic acid alkali metal salt etc. e.g., sodium acetate, in a solvent, e.g., N,N-dimethylformamide or hexamethylphosphoric triamide, to afford compound (30). Removal of the protective group of compound (30) yields compound (31).
4. Compound (25) is reacted with a 1-(p-toluenesulfonyl) alkyl, a 1-benzenesulfonylalkyl, etc. in a solvent, e.g., tetrahydrofuran, in the presence of a base, e.g., n-butyl lithium, simultaneously with removal of the protective group to give compound (32). Compound (32) is reacted with lithium triethylborohydride, etc. in a solvent, e.g., tetrahydrofuran, in the presence of a catalyst, e.g., [1,4-bis(diphenylphosphono)butane]palladium chloride, or reacted with sodium amalgam, etc. in a solvent, e.g., methanol, to obtain compound (33).

EXAMPLES

The present invention will now be illustrated in greater detail with reference to Examples, but it should be understood that the present invention is not deemed to be limited thereto.

The chemical formulae of the compounds prepared in Examples are shown below.

| Example No. | Chemical Formula |
| --- | --- |

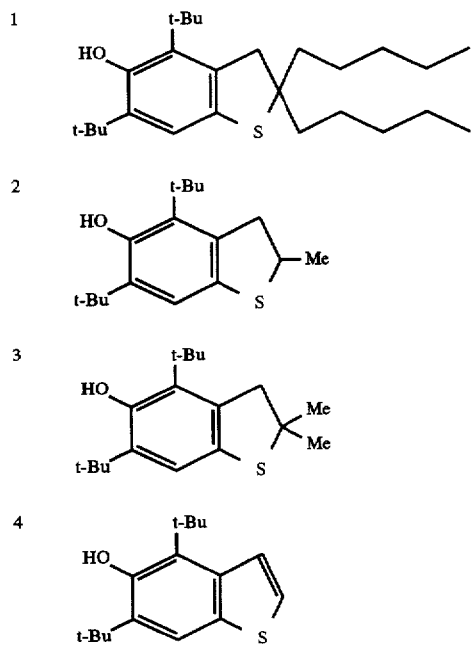

-continued

| Example No. | Chemical Formula |
|---|---|
| 5–12 | 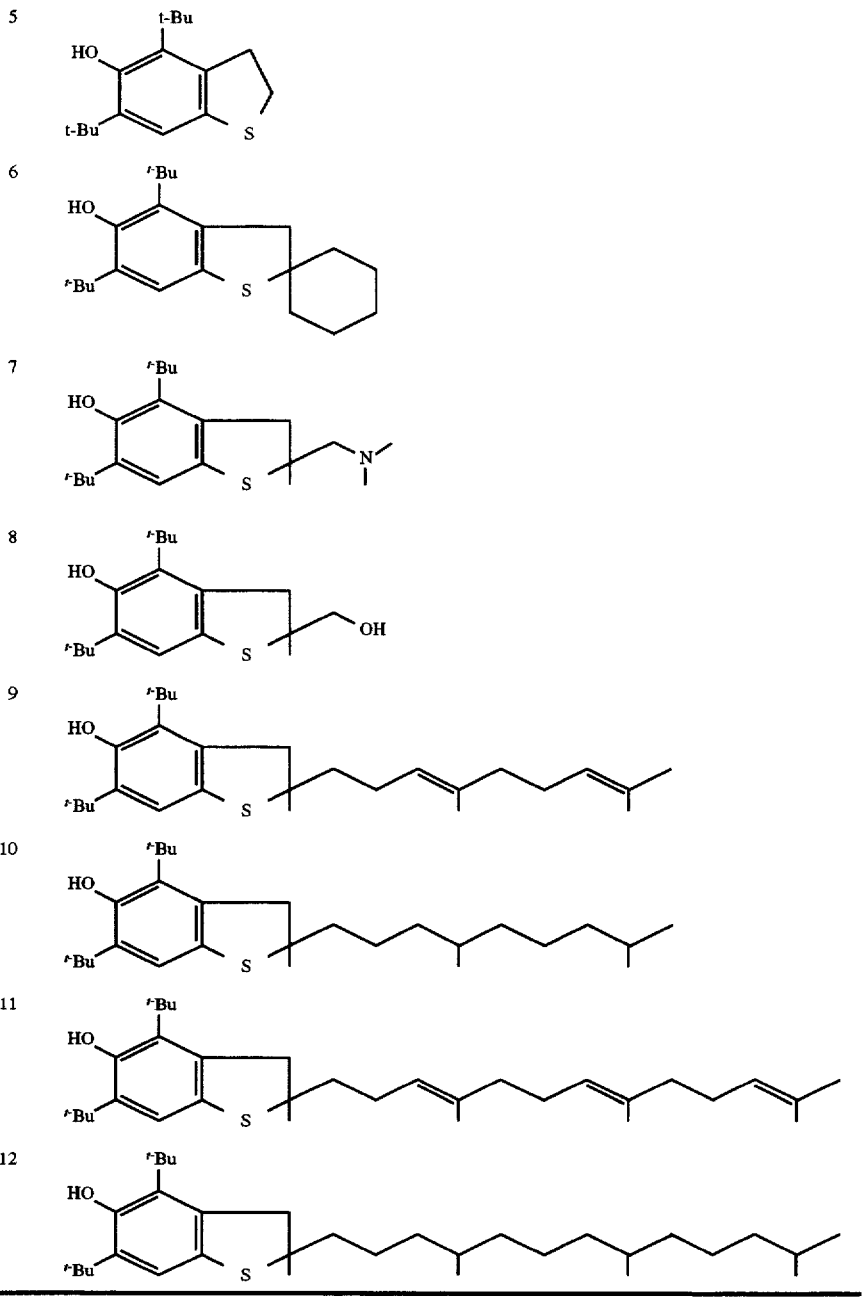 |

Example 1

Synthesis of 4,6-Di-t-butyl-5-hydroxy-2,2-di-n-pentyl-2,3-dihydrobenzothiophene 1) Synthesis of 4-Acetoxy-3,5-di-t-butylanisole In 150 ml of acetic anhydride was dissolved 23.6 g of 4-hydroxy-3,5-di-t-butylanisole, and 0.5 ml of concentrated sulfuric acid was added thereto, followed by stirring at 70° C. for 2 hours. The reaction mixture was concentrated under reduced pressure, and to the residue was added a saturated aqueous solution of sodium hydrogencarbonate. The solution was extracted with ethyl acetate, and the extract was dried over anhydrous magnesium sulfate and concentrated. The precipitated solid was recrystallized from methanol/water (2/1) to give 24.5 g (yield: 88%) of 4-acetoxy-3,5-di-t-butylanisole as a white solid.

$^1$H-NMR (60 Mhz, CDCl$_3$)
δppm: 1.06 (s,18H), 2.02 (s,3H), 3.47 (s,3H), 6.53 (s,2H)
Mass: 278 (M$^+$)
m.p.: 96.6° C.

2) Synthesis of 4-Acetoxy-3,5-di-t-butylphenol

In 2 ml of dichloromethane was dissolved 0.50 g of 4-acetoxy-3,5-di-t-butylanisole, and the solution was cooled with ice. To the solution was added dropwise 0.31 ml of iodotrimethylsilane. The temperature was slowly raised to room temperature, at which the reaction mixture was stirred for 2 days. To the reaction mixture was added a saturated aqueous solution of sodium hydrogencarbonate, and the mixture was extracted with diethyl ether. The organic layer was washed with a saturated sodium chloride aqueous solution and dried over anhydrous magnesium sulfate. After concentration, the residue was purified by silica gel chromatography (15% ethyl acetate in n-hexane) to give 0.38 g (80%) of 4-acetoxy-3,5-di-t-butylphenol as a white solid.

$^1$H NMR (60 Mhz, CDCl$_3$)
δppm: 1.27(s,18H), 2.27(s,3H), 5.22(bs,1H), 6.67(s,2H)
Mass: 222(M$^+$)
m.p.: 156.9° C.

3) Synthesis of 4-Acetoxy-3,5-di-t-butyl-2-(chloroacetylaminomethyl)phenol and 6-Acetoxy-5,7-di-t-butyl-3-(2-chloroacetyl)-2,3-dihydro-1,3,4H-benzoxazine In 200 ml of a 9:1 mixture of acetic acid and sulfuric acid was dissolved 29 g of 4-acetoxy-3,5-di-t-butylphenol, and 34 g of N-hydroxymethyl-2-chloroacetamide was added thereto, followed by stirring at room temperature for 48 hours. The reaction mixture was poured into water, neutralized with a 1N sodium hydroxide aqueous solution, and extracted with ethyl acetate. The organic layer was dried over anhydrous magnesium sulfate and concentrated. The resulting concentrate was used as such in the subsequent reaction. Silica gel chromatography (20% ethyl acetate in n-hexane) of part of the concentrate revealed that the product consisted of 4-acetoxy-3,5-di-t-butyl-2-(chloroacetylaminomethyl)phenol and 6-acetoxy-5,7-di-t-butyl-3-(2-chloroacetyl)-2,3-dihydro-1,3,4H-benzoxazine.

4-Acetoxy-3,5-di-t-butyl-2-(chloroacetylaminomethyl)phenol (colorless oil)
$^1$H NMR (60 MHz, CDCl$_3$)
δppm: 1.30(s,9H), 1.43(s,9H), 2.28(s,3H), 4.00(s,2H), 4.73(d,2H,J=6.0 Hz), 6.88(s,1H), 7.54(t,1H,J=6.0 Hz)
Mass: 369(M$^+$)

6-Acetoxy-5 7-di-t-butyl-3-(2-chloroacetyl)-2,3-dihydro-1,3,4H-benzoxazine (colorless oil)
$^1$H NMR (60 MHz, CDCl$_3$)
δppm: 1.30(s,9H), 1.47(s,9H), 2.30(s,3H), 4.17(s,2H), 5.00(s,2H), 5.33(s,2H), 6.83(s,1H)
Mass: 381(M$^+$)

4) Synthesis of 4-Acetoxy-2-aminomethyl-3,5-di-t-butylphenol

The concentrate obtained in Example 1-3) was dissolved in 550 ml of a 10:3 mixture of ethanol and concentrated hydrochloric acid, and the solution was heated under reflux for 2 hours. After cooling, the reaction mixture was poured into water, neutralized with a 1N sodium hydroxide aqueous solution, and extracted with ethyl acetate. The organic layer was dried over anhydrous magnesium sulfate and concentrated. The resulting concentrate was used as such in the subsequent reaction. Silica gel chromatography (20% ethyl acetate in n-hexane) of part of the concentrate revealed that the product consisted mainly of 4-acetoxy-2-aminomethyl-3,5-di-t-butylphenol.

$^1$H NMR (60 MHz, CDCl$_3$)
δppm: 1.27(s,9H), 1.37(s,9H), 2.25(s,3H), 4.22(s,2H), 5.18(bs,3H), 6.85(s,1H)
Mass: 293(M$^+$)

5) Synthesis of 5-Acetoxy-4,6-di-t-butyl-2-hydroxybenzaldehyde

The concentrate obtained in Example 1-4) was dissolved in 636 ml of a 11:3 mixture of acetic acid and water, and 19.3 g of hexamethylenetetramine was added thereto, followed by heating under reflux for 4 hours. To the reaction mixture was added 85 ml of 4.5N hydrochloric acid, followed by refluxing for additional 20 minutes. After cooling, the reaction mixture was poured into water, neutralized with a 1N sodium hydroxide aqueous solution, and extracted with ethyl acetate. The organic layer was dried over anhydrous magnesium sulfate and concentrated. The concentrate was purified by silica gel column chromatography (chloroform) to afford 19.0 g of 5-acetoxy-4,6-di-t-butyl-2-hydroxybenzaldehyde as a pale yellow solid.

$^1$H-NMR (60 MHz, CDCl$_3$)
δppm: 1.35(s,9H), 1.54(s,9H), 2.35(s,3H), 6.92(s,1H), 10.67(s,1H), 12.32(s,1H)
IR(cm$^{-1}$): 2976, 1758
Mass: 292(M$^+$)
m.p.: 79.0° C.

6) Synthesis of 4-Acetoxy-3,5-di-t-butyl-2-(1-hydroxy-2-n-pentylheptyl)phenol

A solution of 96.4 g of 6-bromoundecane prepared in a usual manner in 300 ml of tetrahydrofuran was added to 10 g of magnesium under a nitrogen atmosphere to prepare a Grignard reagent. To the resulting Grignard reagent was added dropwise a solution of 40 g of 5-acetoxy-4,6-di-t-butyl- 2-hydroxybenzaldehyde in 200 ml of tetrahydrofuran. After stirring the mixture at room temperature for 2 hours, a saturated aqueous solution of ammonium chloride was added to the reaction mixture, followed by extraction with ethyl acetate. The organic layer was dried over anhydrous magnesium sulfate and concentrated. The concentrate was purified by silica gel chromatography (10% ethyl acetate in n-hexane) to yield 24.4 g (39%) of 4-acetoxy-3,5-di-t-butyl-2-(1-hydroxy-2-n-pentylheptyl)phenol as a white solid.

$^1$H NMR (270 MHz, CDCl$_3$)
δppm: 0.91(m,6H), 1.29(s,9H), 1.33(br,16H), 1.40(s,9H), 2.17(m,1H), 2.28(s,3H), 5.22(m,1H), 6.77(s,1H), 7.89(s,1H).
Mass: 448(M$^+$)

7) Synthesis of 4-Acetoxy-3,5-di-t-butyl-2-(2-n-pentyl-1-heptenyl)phenol

To 23.0 g of 4-acetoxy-3,5-di-t-butyl-2-(1-hydroxy-2-n-pentylheptyl)phenol was added 100 g of pyridine, and 4.6 ml of thionyl chloride was added thereto dropwise under cooling with ice. The mixture was stirred at room temperature for 1 hour, and pyridine was removed by evaporation under reduced pressure. Water was added to the residue, and the mixture was extracted with ethyl acetate. The organic layer was dried over anhydrous magnesium sulfate and concentrated. Purification of the concentrate by silica gel chromatography (10% ethyl acetate in n-hexane) gave 19.1 g (87%) of 4-acetoxy-3,5-di-t-butyl-2-(2-n-pentyl-1-heptenyl)phenol as a colorless oil.

$^1$H NMR (60 MHz, CDCl$_3$)
δppm: 0.72–0.99(m,6H), 1.12–1.97(m,14H), 1.30(s,9H), 1.33(s,9H), 2.25(m,2H), 2.27(s,3H), 5.35(d,1H), 6.14(s,1H), 6.85(s,1H)
Mass: 430(M$^+$)

8) Synthesis of O-{4-Acetoxy-3,5-di-t-butyl-2-(2-n-pentyl-1-heptenyl)phenyl}N,N-Dimethylthiocarbamate In 10 ml of N,N-dimethylformamide was suspended 0.14 g of 60% oily sodium hydride under a nitrogen atmosphere, and a solution of 1.25 g of 4-acetoxy-3,5-di -t-butyl-2-(2-n-pentyl-1-heptenyl)phenol in 10 ml of N,N-dimethylformamide was added dropwise to the suspension under cooling with ice, followed by stirring at room temperature for 1 hour. The reaction mixture was cooled with ice, and a solution of 0.43 g of N,N-dimethylthiocarbamoyl chloride in 10 ml of N,N-dimethylformamide was added thereto dropwise. After stirring at room temperature for 1 hour, a saturated aqueous solution of ammonium chloride was added to the reaction mixture, and the mixture was extracted with ethyl acetate. The organic layer was washed successively with water and a saturated aqueous sodium chloride solution, dried over anhydrous magnesium sulfate, and concentrated. The concentrate was purified by silica gel chromatography (10% ethyl acetate in n-hexane) to afford 0.79 g (53%) of O-{4-acetoxy-3,5-di-t-butyl-2-(2-n-pentyl-1-heptenyl)phenyl}N,N-dimethylthiocarbamate as a colorless oil.

$^1$H NMR (270 MHz, CDCl$_3$)

δppm: 0.75(t,3H,J=6.6 Hz), 0.91(t,3H,J=6.8 Hz), 1.11–1.82(m,14H), 1.33(s,9H), 1.35(s,9H), 2.08(t,2H,J=7.8 Hz), 2.32(s,3H), 3.21(s,3H), 3.43(s,3H), 6.14(s,1H), 6.89(s,1H)

Mass: 517(M$^+$)

9) Synthesis of S-{4-Acetoxy-3,5-di-t-butyl-2-(2-n-pentyl-1-heptenyl)phenyl}N,N-Dimethylthiocarbamate In 10 ml of diphenyl ether was dissolved 0.7 g of O-{4-acetoxy-3,5-di-t-butyl-2-(2-n-pentyl-1-heptenyl)phenyl}N,N-dimethylthiocarbamate under a nitrogen atmosphere, followed by heating under reflux for 16 hours. After cooling, the reaction mixture was purified by silica gel chromatography (20% ethyl acetate in n-hexane) to give 0.2 g (29%) of S-{4-acetoxy-3,5-di-t-butyl-2-(2-n-pentyl-1-heptenyl)phenyl}N,N-dimethylthiocarbamate as a colorless oil.

$^1$H NMR (270 MHz, CDCl$_3$)

δppm: 0.74(t,3H,J=6.8 Hz), 0.91(t,3H,J=7.0 Hz), 1.08–1.76(m,14H), 1.33(s,9H), 1.35(s,9H), 2.12(t,2H,J=7.4 Hz), 2.31(s,3H), 3.04(s,6H), 6.31(s,1H), 7.41(s,1H)

Mass: 517(M$^+$)

10) Synthesis of 5-Acetoxy-4,6-di-t-butyl-2,2-di-n-pentyl-2,3-dihydrobenzothiophene To 0.2 g of S-{4-acetoxy-3,5-di-t-butyl-2-(2-n-pentyl-1-heptenyl)phenyl}N,N-dimethylthiocarbamate was added 10 ml of boron trifluoride etherate under a nitrogen atmosphere, followed by stirring at room temperature for 3 hours. The reaction mixture was poured into a saturated aqueous solution of sodium hydrogencarbonate and extracted with chloroform. The organic layer was dried over anhydrous magnesium sulfate and concentrated. The concentrate was purified by silica gel chromatography (10% ethyl acetate in n-hexane) to provide 0.1 g (57%) of 5-acetoxy-4,6-di-t-butyl-2,2-di-n-pentyl-2,3-dihydrobenzothiophene as a colorless oil.

$^1$H NMR (270 MHz, CDCl$_3$)

δppm: 0.88(m,6H), 1.29(s,9H), 1.30(br,12H), 1.38(s,9H), 1.76(m,4H), 2.28(s,3H), 3.26(d,1H,J=15.2 Hz), 3.33(d,1H,J=15.2 Hz), 7.07(s,1H)

Mass: 446(M$^+$)

11) Synthesis of 4,6-Di-t-butyl-5-hydroxy-2,2-di-n-pentyl-2,3-dihydrobenzothiophene In 10 ml of tetrahydrofuran was suspended 0.07 g of lithium aluminum hydride under a nitrogen atmosphere, and a solution of 0.85 g of 5-acetoxy-4,6-di-t-butyl-2,2-di-n-pentyl-2,3-dihydrobenzothiophene in 10 ml of tetrahydrofuran was added dropwise to the suspension. The mixture was heated under reflux for 3 hours and cooled to room temperature. A 10% hydrochloric acid aqueous solution was added to the reaction mixture, followed by extraction with ethyl acetate. The organic layer was washed with a saturated sodium chloride aqueous solution, dried over anhydrous magnesium sulfate, and concentrated. The concentrate was purified by silica gel chromatography (n-hexane) to give 0.55 g (72%) of 4,6-di-t-butyl-5-hydroxy-2,2-di-n-pentyl-2,3-dihydrobenzothiophene as a colorless oil.

$^1$H NMR (270 MHz, CDCl$_3$)

δppm: 0.88(t,6H,J=6.8 Hz), 1.29(br,12H), 1.39(s,9H), 1.52(s,9H), 1.73(m,4H), 3.33(s,2H), 5.08(s,1H), 6.95(s,1H)

IR(cm$^{-1}$): 3648, 2952

Mass: 404(M$^+$)

Example 2

Synthesis of 4,6-Di-t-butyl-5-hydroxy-2-methyl-2,3-dihydrobenzothiophene

1) Synthesis of 4-Acetoxy-3,5-di-t-butyl-1-(2-propenyloxy)benzene

In 300 ml of acetone was dissolved 10 g of 4-acetoxy-3,5-di-t-butylphenol obtained in Example 1-2) and 15.6 g of potassium carbonate, and 0.39 ml of 3-bromo-1-propene was added thereto, followed by refluxing for 24 hours. The reaction mixture was concentrated under reduced pressure, water was added to the residue, and the mixture was extracted with diethyl ether. The organic layer was washed successively with water and a saturated sodium chloride aqueous solution, dried over anhydrous magnesium sulfate, and concentrated. The concentrate was purified by silica gel chromatography (10% ethyl acetate in n-hexane) to quantitatively provide 11.0 g of 4-acetoxy-3,5-di-t-butyl-1-(2-propenyloxy)benzene as a colorless oil.

$^1$H NMR (60 MHz, CDCl$_3$)

δppm: 1.30(s,18H), 2.27(s,3H), 4.47(d,2H,J=5.0 Hz), 5.05–5.57(m,2H), 5.68–6.37(m,1H), 6.81(s,2H)

Mass: 304(M$^+$)

2) Synthesis of 4-Acetoxy-3,5-di-t-butyl-2-(2-propenyl)phenol

In 50 ml of N,N-dimethylaniline was dissolved 11.0 g of 4-acetoxy-3,5-di-t-butyl-1-(2-propenyloxy)benzene, and the solution was heated under reflux for 18 hours under a nitrogen atmosphere. After cooling to room temperature, the reaction mixture was concentrated under reduced pressure, and the concentrate was purified by silica gel chromatography (15% ethyl acetate in n-hexane) to give 8.84 g (77%) of 4-acetoxy-3,5-di-t-butyl-2-(2-propenyl)phenol as a white solid.

$^1$H NMR (60 MHz, CDCl$_3$)

δppm: 1.30(s,9H), 1.42(s,9H), 2.28(s,3H), 3.52–3.84(m,2H), 4.88–5.42(m,3H), 5.68–6.45(m,1H), 6.79(s,1H)

Mass: 304(M$^+$)

m.p.: 103.6° C.

3) Synthesis of O-{4-Acetoxy-3,5-di-t-butyl-2-(2-propenyl)phenyl}N,N-Dimethylthiocarbamate In 10 ml of N,N-dimethylformamide was suspended 0.32 g of 60% oily sodium hydride under a nitrogen atmosphere. A solution of 2.0 g of 4-acetoxy-3,5-di-t-butyl-2-(2-propenyl)phenol in 10 ml of N,N-dimethylformamide was added dropwise to the suspension while cooling with ice, followed by stirring at room temperature for 1 hour. The reaction mixture was cooled with ice, and a solution of 0.99 g of N,N-dimethylthiocarbamoyl chloride in 10 ml of N,N-dimethylformamide was added thereto dropwise. After stirring at room temperature for 1 hour, a saturated aqueous solution of ammonium chloride was added to the reaction mixture, and the mixture was extracted with ethyl acetate. The organic layer was washed successively with water and a saturated aqueous solution of sodium chloride, dried over anhydrous magnesium sulfate, and concentrated. The concentrate was purified by silica gel chromatography (10% ethyl acetate in n-hexane) to afford 2.05 g (79%) of O-{4-acetoxy-3,5-di-t-butyl-2-(2-propenyl)phenyl}N,N-dimethylthiocarbamate as a white solid.

$^1$H NMR (60 MHz, CDCl$_3$)

δppm: 1.33(s,9H), 1.43(s,9H), 2.30(s,3H), 3.27(s,3H), 3.42(s,3H), 3.62(m,2H), 4.72–5.05(m,2H), 5.63–6.18(m,1H), 6.95(s,1H)

Mass: 391(M$^+$)

m.p.: 134.3° C.

4) Synthesis of S-{4-Acetoxy-3,5-di-t-butyl-2-(2-propenyl)phenyl}N,N-Dimethylthiocarbamate In 10 ml of diphenyl ether was dissolved 1.0 g of O-{4-acetoxy-3,5-di-t-butyl-2-(2-propenyl)phenyl}N,N-dimethylthiocarbamate under a nitrogen atmosphere, and the solution was heated under reflux for 16 hours. After cooling, the reaction mixture was purified by silica gel chromatography (20% ethyl acetate in n-hexane) to give 0.74 g (74%) of S-{4-acetoxy-3,5-di-t-butyl-2-(2-propenyl)phenyl}N,N-dimethylthiocarbamate as a white solid.

$^1$H NMR (270 MHz, CDCl$_3$)

δppm: 1.33(s,9H), 1.43(s,9H), 2.31(s,3H), 3.05(bs,6H), 3.88(d,2H,J=5.0 Hz), 4.71(d,1H,J=17.2 Hz), 5.00(d,1H,J=10.2 Hz), 5.83–6.00(m,1H), 7.42(s,1H)

Mass: 391(M$^+$)

m.p.: 133.6° C.

5) Synthesis of 4,6-Di-t-butyl-5-hydroxy-2-methyl-2,3-dihydrobenzothiophene

In 10 ml of tetrahydrofuran was suspended 0.14 g of lithium aluminum hydride under a nitrogen atmosphere, and a solution of 0.7 g of S-{4-acetoxy-3,5-di-t-butyl-2-(2-propenyl)phenyl}N,N-dimethylthiocarbamate in 10 ml of tetrahydrofuran was added dropwise to the suspension. The mixture was heated under reflux for 3 hours and cooled to room temperature. To the reaction mixture was added carefully 10 ml of acetic acid, and the mixture was refluxed for additional 30 minutes. After cooling, a 10% hydrochloric acid aqueous solution was added to the reaction mixture, and the mixture was extracted with ethyl acetate. The organic layer was washed with a saturated sodium chloride aqueous solution, dried over anhydrous magnesium sulfate, and concentrated. The concentrate was purified by silica gel chromatography (5% ethyl acetate in n-hexane) to yield 0.35 g (70%) of 4,6-di-t-butyl-5-hydroxy-2-methyl-2,3-dihydrobenzothiophene as a white solid.

$^1$H NMR (270 MHz, CDCl$_3$)

δppm: 1.39(s,9H), 1.42(d,3H,J=6.6 Hz), 1.52(s,9H), 3.17(m,1H), 3.64(m,1H), 3.80(m,1H), 5.11(s,1H), 7.01(s,1H)

IR(cm$^{-1}$): 3620, 2956

Mass: 278(M$^+$)

m.p.: 96.7° C.

Example 3

Synthesis of 4,6-Di-t-butyl-5-hydroxy-2,2-dimethyl-2,3-dihydrobenzothiophene

1) Synthesis of 4-Acetoxy-3,5-di-t-butyl-1-(2-methyl-2-propenyloxy)benzene

In 10 ml of N,N-dimethylformamide was suspended 0.18 g of 60% oily sodium hydride under a nitrogen atmosphere, and a solution of 1.0 g of 4-acetoxy-3,5-di -t-butylphenol obtained in Example 1-2) in 5 ml of N,N -dimethylformamide was added thereto dropwise under cooling with ice, followed by stirring for 30 minutes. The temperature was raised to room temperature, 0.45 ml of 3-chloro-2-methyl-1-propene was added thereto dropwise, and the reaction mixture was stirred at room temperature for 2 hours. To the reaction mixture was added 15 ml of a saturated aqueous solution of ammonium chloride, followed by extraction with diethyl ether. The organic layer was washed successively with water and a saturated sodium chloride aqueous solution, dried over anhydrous magnesium sulfate, and concentrated. The concentrate was purified by silica gel chromatography (10% ethyl acetate in n-hexane) to give 1.08 g (90%) of 4-acetoxy-3,5-di-t-butyl-1-(2-methyl-2-propenyloxy)benzene as a colorless oil.

$^1$H NMR (60 MHz, CDCl$_3$)

δppm: 1.30(s,18H), 1.83(s,3H), 2.30(s,3H), 4.37(s,2H), 5.02(br,2H), 6.83(s,2H)

Mass: 318(M$^+$)

2) Synthesis of 4-Acetoxy-3,5-di-t-butyl-2-(2-methyl-2-propenyl)phenol

In 100 ml of N,N-dimethylaniline was dissolved 24.0 g of 4-acetoxy-3,5-di-t-butyl-1-(2-methyl-2-propenyl-oxy)benzene, and the solution was heated under reflux for 18 hours under a nitrogen atmosphere. After cooling to room temperature, the reaction mixture was concentrated under reduced pressure, and the concentrate was purified by silica gel chromatography (10% ethyl acetate in n-hexane) to give 6.66 g (28%) of 4-acetoxy-3,5-di-t-butyl-2-(2-methyl-2-propenyl)phenol as a white solid.

$^1$H NMR (60 MHz, CDCl$_3$)

δppm: 1.30(s,9H), 1.37(s,9H), 1.88(s,3H), 2.28(s,3H), 3.34(br,2H), 4.60(bs,1H), 4.88(bs,1H), 5.02(bs,1H), 6.79(s, 1H)

Mass: 318(M$^+$)

m.p.: 102.0° C.

3) Synthesis of O-{4-Acetoxy-3,5-di-t-butyl-2-(2-methyl-2-propenyl)phenyl}N,N-Dimethylthiocarbamate In 20 ml of N,N-dimethylformamide was suspended 0.75 g of 60% oily sodium hydride under a nitrogen atmosphere. A solution of 4.57 g of 4-acetoxy-3,5-di-t-butyl-2-(2-methyl-2-propenyl)phenol in 20 ml of N,N-dimethylformamide was added dropwise to the suspension under ice-cooling, followed by stirring at room temperature for 1 hour. The reaction mixture was cooled with ice, and a solution of 1.82 g of N,N-dimethylthiocarbamoyl chloride in 20 ml of N,N-dimethylformamide was added thereto dropwise. After stirring at room temperature for 1 hour, a saturated ammonium chloride aqueous solution was added to the reaction mixture, and the mixture was extracted with ethyl acetate. The organic layer was washed successively with water and a saturated sodium chloride aqueous solution, dried over anhydrous magnesium sulfate, and concentrated. The concentrate was purified by silica gel chromatography (10% ethyl acetate in n-hexane) to afford 3.04 g (52%) of O-{4-acetoxy-3,5-di-t-butyl-2-(2-methyl-2-propenyl)phenyl} N,N-dimethylthiocarbamate as a white solid.

$^1$H NMR (270 MHz, CDCl$_3$)

δppm: 1.33(s,9H), 1.40(s,9H), 1.77(s,3H), 2.31(s,3H), 3.25(s,3H), 3.29–3.60(m,2H), 3.45(s,3H), 4.29(bs,1H), 4.76(bs,1H), 6.96(s,1H)

Mass: 405(M$^+$)

m.p.: 152.1° C.

4) Synthesis of S-{4-Acetoxy-3,5-di-t-butyl-2-(2-methyl-2-propenyl)phenyl}N,N-Dimethylthiocarbamate In 10 ml of diphenyl ether was dissolved 1.0 g of O-{4-acetoxy-3,5-di-t-butyl-2-(2-methyl-2-propenyl)phenyl}N,N-dimethylthiocarbamate under a nitrogen atmosphere, and the solution was heated under reflux for 16 hours. After cooling, the reaction mixture was purified by silica gel chromatography (20% ethyl acetate in n-hexane) to afford 0.57 g (57%) of S-{4-acetoxy-3,5-di-t-butyl-2-(2-methyl-2-propenyl)phenyl}N,N-dimethylthiocarbamate as a white solid.

$^1$H NMR (270 MHz, CDCl$_3$)

δppm: 1.33(s,9H), 1.40(s,9H), 1.83(s,3H), 2.31(s,3H), 3.06(bs,6H), 3.70(m,2H), 4.00(bs,1H), 4.74(bs,1H), 7.41(s, 1H)

Mass: 405(M$^+$)

m.p.: 132.1° C.

5) Synthesis of 4,6-Di-t-butyl-5-hydroxy-2,2-dimethyl-2,3-dihydrobenzothiophene

In 10 ml of tetrahydrofuran was suspended 0.1 g of lithium aluminum hydride under a nitrogen atmosphere, and a solution of 0.5 g of S-{4-acetoxy-3,5-di-t-butyl-2-(2-methyl-2-propenyl)phenyl}N,N-dimethylthiocarbamate in 10 ml of tetrahydrofuran was added thereto dropwise, followed by heating under reflux for 3 hours. After cooling to room temperature, 10 ml of acetic acid was carefully added to the reaction mixture, followed by refluxing for 30 minutes. After cooling, a 10% hydrochloric acid aqueous solution was added thereto, and the mixture was extracted with ethyl acetate. The organic layer was washed with a saturated sodium chloride aqueous solution, dried over anhydrous magnesium sulfate, and concentrated. The concentrate was purified by silica gel chromatography (5% ethyl acetate in n-hexane) to give 0.25 g (70%) of 4,6-di-t-butyl-5-hydroxy-2,2-dimethyl-2,3-dihydrobenzothiophene as a white solid.

$^1$H NMR (270 MHz, CDCl$_3$)

δppm: 1.39(s,9H), 1.51(s,6H), 1.52(s,9H), 3.34(s,2H), 5.11(s,1H), 6.98(s,1H)

IR(cm$^{-1}$): 3644, 2956

Mass: 292(M$^+$)

m.p.: 79.0° C.

Example 4

Synthesis of 4,6-Di-t-butyl-5-hydroxybenzo[b] thiophene

1) Synthesis of S-(4-Acetoxy-3,5-di-t-butyl-2-formylmethylphenyl) N,N-Dimethylthiocarbamate In 20 ml of a 3:1 mixture of tetrahydrofuran and water was dissolved 1.0 g of S-{4-acetoxy-3,5-di-t-butyl-2-(2-propenyl)phenyl}N,N-dimethylthiocarbamate prepared in Example 2-4), and 50 mg of osmium tetroxide and 1.1 g of sodium periodate were added to the solution, followed by stirring at room temperature for 24 hours. A saturated aqueous solution of sodium thiosulfate was added to the reaction mixture, and the mixture was extracted with ethyl acetate. The organic layer was washed with a saturated aqueous solution of sodium chloride, dried over anhydrous magnesium sulfate, and concentrated. The concentrate was purified by silica gel chromatography (20% ethyl acetate in n-hexane) to give 0.52 g (52%) of S-(4-acetoxy-3,5-di-t-butyl-2-formylmethylphenyl) N,N-dimethylthiocarbamate as a white solid.

$^1$H NMR (60 MHz, CDCl$_3$)

δppm: 1.30(s,9H), 1.43(s,9H), 2.33(s,3H), 3.01(s,6H), 4.10(bs,2H), 7.47(s,1H), 9.62(bs,1H)

Mass: 393(M$^+$)

2) Synthesis of 5-Acetoxy-4,6-di-t-butylbenzo[b]thiophene

In 15 ml of benzene was dissolved 0.5 g of S-(4-acetoxy-3,5-di-t-butyl-2-formylmethylphenyl) N,N-dimethylthiocarbamate, and a catalytic amount of p-toluenesulfonic acid was added thereto, followed by heating under reflux for 1 hour. After cooling, a saturated aqueous solution of sodium hydrogencarbonate was added to the reaction mixture, and the mixture was extracted with ethyl acetate. The organic layer was dried over anhydrous magnesium sulfate and concentrated. The concentrate was purified by silica gel chromatography (10% ethyl acetate in n-hexane) to give 0.3 g (78%) of 5-acetoxy-4,6-di-t-butylbenzo[b]thiophene as a colorless oil.

$^1$H NMR (60 MHz, CDCl$_3$)

δppm: 1.37(s,9H), 1.54(s,9H), 2.31(s,3H), 7.28(d,1H,J=6.0 Hz), 7.62(d,1H,J=6.0 Hz), 7.72(s,1H)

Mass: 304(M$^+$)

3) Synthesis of 4,6-Di-t-butyl-5-hydroxybenzo[b]thiophene

In 10 ml of tetrahydrofuran was suspended 0.11 g of lithium aluminum hydride under a nitrogen atmosphere, and a solution of 0.9 g of 5-acetoxy-4,6-di-t-butyl-benzo[b]thiophene in 10 ml of tetrahydrofuran was added thereto dropwise. The mixture was heated under reflux for 3 hours, followed by cooling to room temperature. A 10% hydrochloric acid aqueous solution was added thereto, and the mixture was extracted with ethyl acetate. The organic layer was washed with a saturated sodium chloride aqueous solution, dried over anhydrous magnesium sulfate, and concentrated. The concentrate was purified by silica gel chromatography (n-hexane) to yield 0.7 g (90%) of 4,6-di-t-butyl-5-hydroxybenzo[b]thiophene as a pale yellow solid.

$^1$H NMR (270 MHz, CDCl$_3$)

δppm: 1.48(s,9H), 1.71(s,9H), 5.64(s,1H), 7.31(d,1H,J=5.9 Hz), 7.66(s,1H), 7.72(d,1H,J=5.9 Hz)

IR(cm$^{-1}$): 3644, 2952

Mass: 262(M$^+$)

m.p.: 107.4° C.

Example 5

Synthesis of 4,6-Di-t-butyl-5-hydroxy-2,3-dihydrobenzothiophene

1) Synthesis of 5-Acetoxy-4,6-di-t -butyldioxobenzo[b] thiophene 1,1-Dioxide

In 2 ml of acetic acid was dissolved 0.3 g of 5-acetoxy-4,6-di-t-butylbenzo[b]thiophene obtained in Example 4-2), and 2.2 ml of a 35% hydrogen peroxide aqueous solution was added thereto, followed by heating under reflux for 1 hour. After cooling, water was added thereto, and the mixture was extracted with ethyl acetate. The organic layer was washed with a saturated aqueous solution of sodium chloride, dried over anhydrous magnesium sulfate, and concentrated. The concentrate was purified by silica gel chromatography (50% ethyl acetate in n-hexane) to give 0.3 g (89%) of 5-acetoxy-4,6-di-t-butylbenzo[b]thiophene 1,1-dioxide as a white solid.

$^1$H NMR (60 MHz, CDCl$_3$)

δppm: 1.35(s,9H), 1.43(s,9H), 2.33(s,3H), 6.63(d,1H,J=7.0 Hz), 7.56(s,1H), 7.68(d,1H,J=7.0 Hz)

Mass: 336(M$^+$)

m.p.: 195.0° C.

2) Synthesis of 5-Acetoxy-4,6-di-t-butyl-2,3-dihydrobenzothiophene 1,1-Dioxide

To a solution of 0.3 g of 5-acetoxy-4,6-di-t -butylbenzo[b]thiophene 1,1-dioxide in 10 ml of ethyl acetate was added 0.03 g of 10% palladium-on-carbon, and the mixture was stirred under a hydrogen atmosphere for 24 hours. After palladium-on-carbon was separated by filtration, the filtrate was concentrated, and the concentrate was purified by silica gel chromatography (50% ethyl acetate in n-hexane) to give 0.27 g (90%) of 5-acetoxy-4,6-di-t-butyl-2,3-dihydrobenzothiophene 1,1-dioxide as a white solid.

$^1$H NMR (270 MHz, CDCl$_3$)

δppm: 1.35(s,9H), 1.44(s,9H), 2.36(s,3H), 3.33–3.69(m, 4H), 7.65(s,1H)

Mass: 338(M$^+$)

m.p.: 182.0° C.

3) Synthesis of 4,6-Di-t-butyl-5-hydroxy-2,3-dihydrobenzothiophene

In 10 ml of tetrahydrofuran was suspended 0.15 g of lithium aluminum hydride under a nitrogen atmosphere. A solution of 0.27 g of 5-acetoxy-4,6-di-t-butyl-2,3-dihydrobenzothiophene 1,1-dioxide in 10 ml of tetrahydrofuran was added to the suspension dropwise, followed by heating under reflux for 3 hours. After cooling to room temperature, a 10% hydrochloric acid aqueous solution was added to the reaction mixture, and the mixture was extracted with ethyl acetate. The organic layer was washed with a saturated sodium chloride aqueous solution, dried over anhydrous magnesium sulfate, and concentrated. The concentrate was purified by silica gel chromatography (n-hexane) to give 10 mg of 4,6-di-t-butyl-5-hydroxy-2,3-dihydrobenzothiophene as a pale yellow solid.

$^1$H NMR (270 MHz, CDCl$_3$)

δppm: 1.41(s,9H), 1.54(s,9H), 3.22(t,2H,J=7.6 Hz), 3.53 (t,2H,J=7.6 Hz), 5.13(s,1H), 7.08(s,1H)

IR(cm$^{-1}$): 3640, 2956

Mass: 264(M$^+$)

m.p.: 82.0° C.

Example 6

Synthesis of 4,6-Di-t-butyl-5-hydroxy-2,3-dihydrobenzothiophene-2-spiro-1'-cyclohexane The title compound was obtained in the same manner as in Example 1.

$^1$H NMR (270 MHz, CDCl$_3$)

δppm: 1.39(s,9H), 1.45–1.65(m,10H), 1.53(s,9H), 3.34(s, 2H), 5.10(s,1H), 6.96(s,1H)

IR(cm$^{-1}$): 3644, 3620, 2924

Mass: 332(M$^+$)

m.p.: 128.5° C.

Example 7

Synthesis of 4,6-Di-t-butyl-5-hydroxy-2-(N,N-dimethylaminomethyl)-2-methyl-2,3-dihydrobenzothiophene 1) Synthesis of 5-Acetoxy-4,6-di-t-butyl-2-iodomethyl-2-methyl-2,3-dihydrobenzothiophene In 400 ml of a 3:1 mixture of diethyl ether and water was dissolved 40 g of S-{4-acetoxy-3,5-di-t-butyl-2-(2-methyl-2-propenyl)phenyl}N,N-dimethylthiocarbamate obtained in Example 3-4), and 16.6 g of sodium hydrogencarbonate and 37.7 g of iodine were added to the solution, followed by stirring at room temperature for 30 minutes. A saturated aqueous solution of sodium thiosulfate was added to the reaction mixture, and the mixture was extracted with ethyl acetate. The organic layer was washed with a saturated sodium chloride aqueous solution, dried over anhydrous magnesium sulfate, and concentrated to give 45.3 g (99%) of 5-acetoxy-4,6-di-t-butyl-2-iodomethyl-2-methyl-2,3-dihydrobenzothiophene as a pale yellow oil.

$^1$H NMR (270 MHz, CDCl$_3$)

δppm: 1.29(s,9H), 1.42(d,9H,J=0.7 Hz), 1.69(d,3H,J=6.9 Hz), 2.30(d,3H,J=2.0 Hz), 3.17(dd,1H,J=15.2 Hz,J=1.3 Hz), 3.52–3.72(m,2H), 3.79(d,1H,J=15.2 Hz), 7.07(d,1H,J=4.3 Hz)

Mass: 460(M$^+$)

2) Synthesis of 5-Acetoxy-4,6-di-t-butyl-2-(N,N-dimethylaminomethyl)-2-methyl-2,3-dihydrobenzothiophene In 40 ml of a 3:1 mixture of N,N-dimethylformamide and water was dissolved 2.0 g of 5-acetoxy-4,6-di-t-butyl-2-iodomethyl-2-methyl-2,3-dihydrobenzothiophene. To the solution were added 2.47 g of N,N-dimethylamine hydrochloride and 4.2 g of potassium carbonate, and the mixture was stirred at room temperature for 24 hours. Water was added to the reaction mixture, and the mixture was extracted with n-hexane. The organic layer was washed with a saturated sodium chloride aqueous solution, dried over anhydrous magnesium sulfate, and concentrated. The concentrate was purified by silica gel chromatography (33% ethyl acetate in n-hexane) to give 1.6 g (98%) of 5-acetoxy-4,6-di-t-butyl-2-(N,N-dimethylaminomethyl)-2-methyl-2,3-dihydrobenzothiophene as a colorless oil.

$^1$H NMR (270 MHz, CDCl$_3$)

δppm: 1.29(s,9H), 1.39(s,9H), 1.54(d,3H,J=18.5 Hz), 2.29(s,3H), 2.34(s,3H), 2.37(s,3H), 2.56(d,1H,J=5.9 Hz), 2.66(d,1H,J=4.9 Hz), 3.21(dd,1H,J=15.2 Hz,J=5.9 Hz), 3.44 (dd,1H,J=17.5 Hz,J=15.2 Hz), 7.08(d,1H,J=3.3 Hz)

Mass: 377(M$^+$)

3) Synthesis of 4,6-Di-t-butyl-5-hydroxy-2-(N,N-dimethylaminomethyl)-2-methyl-2,3-dihydrobenzothiophene In 10 ml of tetrahydrofuran was suspended 0.16 g of lithium aluminum hydride under a nitrogen atmosphere, and a solution of 1.6 g of 5-acetoxy-4,6-di-t-butyl-2-(N,N-dimethylaminomethyl)-2-methyl-2,3-dihydrobenzothiophene in 30 ml of tetrahydrofuran was added dropwise thereto. The mixture was heated under reflux for 3 hours and cooled to room temperature. A saturated ammonium chloride aqueous solution was added to the reaction mixture, and the mixture was extracted with ethyl acetate. The organic layer was washed with a saturated sodium chloride aqueous solution, dried over anhydrous magnesium sulfate, and concentrated. The concentrate was purified by silica gel chromatography (20% ethyl acetate in n-hexane) to give 1.29 g (91) of 4,6-di-t-butyl-5-hydroxy-2-(N,N-dimethylaminomethyl)-2-methyl-2,3-dihydrobenzothiophene as a colorless oil.

$^1$H NMR (270 MHz, CDCl$_3$)

δppm: 1.39(s,9H), 1.52(s,3H), 1.53(s,9H), 2.35(s,6H), 2.52(d,1H,J=13.5 Hz), 2.58(d,1H,J=13.5 Hz), 3.19(d,1H,J=15.2 Hz), 3.55(d,1H,J=15.2 Hz), 5.09(s,1H), 6.96(s,1H)

IR(cm$^{-1}$): 3640, 2960

Mass: 335(M$^+$)

Example 8

Synthesis of 4,6-Di-t-butyl-5-hydroxy-2-hydroxymethyl-2-methyl-2,3-dihydrobenzothiophene 1) Synthesis of 5-Acetoxy-2-acetoxymethyl-4,6-di-t-butyl-2-methyl-2,3-dihydrobenzothiophene In 30 ml of hexamethylphosphoric triamide was dissolved 2.0 g of 5-acetoxy-4,6-di-t-butyl-2-iodomethyl-2-methyl-2,3-dihydrobenzothiophene prepared in Example 7-1), and 0.71 g of sodium acetate was added thereto, followed by stirring at room temperature for 24 hours. Water was added to the reaction mixture, and the mixture was extracted with ethyl acetate. The organic layer was washed with a saturated sodium chloride aqueous solution, dried over anhydrous magnesium sulfate, and concentrated. The concentrate was purified by silica gel chromatography (20% ethyl acetate in n-hexane) to afford 1.0 g (59%) of 5-acetoxy-2-acetoxymethyl-4,6-di-t-butyl-2-methyl-2,3-dihydrobenzothiophene as a colorless oil.

$^1$H NMR (270 MHz, CDCl$_3$)

δppm: 1.29(s,9H), 1.38(d,9H,J=1.0 Hz), 1.56(d,3H,J=3.3 Hz), 2.05(d,3H,J=15.2 Hz), 2.29(s,3H), 3.24(dd,1H,J=25.4 Hz,J=15.2 Hz), 3.57(dd,1H,J=18.1 Hz,J=15.2 Hz), 4.16(dd, 1H,J=37.3 Hz,J=11.2 Hz), 4.18(s,1H), 7.08(d,1H,J=1.7 Hz)

Mass: 392(M$^+$)

2) Synthesis of 4,6-Di-t-butyl-5-hydroxy-2-hydroxymethyl-2-methyl-2,3-dihydrobenzothiophene In 10 ml of tetrahydrofuran was suspended 0.14 g of lithium aluminum hydride under a nitrogen atmosphere, and a solution of 0.6 g of 5-acetoxy-2-acetoxymethyl-4,6-di-t-butyl-2-methyl-2,3-dihydrobenzothiophene in 20 ml of tetrahydrofuran was added dropwise to the suspension. The mixture was heated under reflux for 3 hours and cooled to room temperature. A 10% aqueous solution of hydrochloric acid was added thereto, and the mixture was extracted with ethyl acetate. The organic layer was washed with a saturated aqueous solution of sodium chloride, dried over anhydrous magnesium sulfate, and concentrated. The concentrate was purified by silica gel chromatography (20% ethyl acetate in n-hexane) to give 0.39 g (84%) of 4,6-di-t-butyl-5-hydroxy-2-hydroxymethyl-2-methyl-2,3-dihydrobenzothiophene as a colorless oil.

$^1$H NMR (270 MHz, CDCl$_3$)

δppm: 1.39(s,9H), 1.52(s,9H), 1.53(s,3H), 1.98(t,1H,J=6.6 Hz), 3.25(d,1H,J=15.5 Hz), 3.46–3.60(m,2H), 3.59(d, 1H,J=15.5 Hz), 5.15(s,1H), 6.96(s,1H)

IR(cm$^{-1}$): 3640, 3432, 2956

Mass: 308(M$^+$)

Example 9

Synthesis of 4,6-Di-t-butyl-5-hydroxy-2-methyl-2-(4,8-dimethylnona-3(E),7-dienyl)-2,3-dihydrobenzothiophene 1) Synthesis of 4,6-Di-t-butyl-5-hydroxy-2-methyl-2-(4,8-dimethyl-2-p-toluenesulfonylnona-3(E),7-dienyl)-2,3-dihydrobenzothiophene In 12 ml of a 4:1 mixture of tetrahydrofuran and hexamethylphosphoric triamide was dissolved 1.52 g of 3,7-dimethyl-1-(p-toluenesulfonyl)-2(E),6-octadiene prepared according to Gosselin, P. et al., Synthesis, 876 (1984). To the resulting solution was added dropwise 3.42 ml of a 1.6M n-pentane solution of n-butyl lithium at –78° C., followed by stirring for 2 hours. Then, a solution of 2.0 g of 5-acetoxy-4,6-di-t-butyl-2-iodomethyl-2-methyl-2,3-dihydrobenzothiophene obtained in Example 7-1) in 10 ml of tetrahydrofuran was added thereto dropwise, followed by stirring for 4 hours. After completion of the reaction, a saturated ammonium chloride aqueous solution was added to the reaction mixture, and the mixture was extracted with ethyl acetate. The organic layer was washed with a saturated sodium chloride aqueous solution, dried over anhydrous magnesium sulfate, and concentrated. The concentrate was purified by silica gel chromatography (10% ethyl acetate in n-hexane) to provide 0.5 g of 4,6-di-t -butyl-5-hydroxy-2-methyl-2-(4,8-dimethyl-2-p-toluenesulfonylnona-3(E),7-dienyl)-2,3-dihydrobenzothiophene (a mixture of diastereomers) as a pale yellow oil.

$^1$H NMR (270 MHz, CDCl$_3$)

δppm: 1.12–1.73(m,12H), 1.37(s,4.5H), 1.38(s,4.5H), 1.50(s,9H), 1.89–2.08(m,4H), 2.42(s,1.5H), 2.44(s,1.5H), 2.69–2.76(m,2H), 3.26–3.51(m,2H), 3.95–4.06(m,1H), 5.03–5.07(m,2H), 5.11(s,0.5H), 5.12(s,0.5H), 6.89(s,0.5H), 6.90(s,0.5H), 7.25–7.32(m,2H), 7.64–7.76(m,2H)

IR(cm$^{-1}$): 3636, 2920

Mass: 582(M$^+$)

2) Synthesis of 4,6-Di-t-butyl-5-hydroxy-2-methyl-2-(4,8-dimethylnona-3(E),7-dienyl)-2,3-dihydrobenzothiophene In 4 ml of tetrahydrofuran was dissolved 0.5 g of 4,6-di-t-butyl-5-hydroxy-2-methyl-2-(4,8-dimethyl-2-p-toluenesulfonylnona-3(E),7-dienyl)-2,3-dihydrobenzothiophene under a nitrogen atmosphere, and 48 mg of [1,4-bis(diphenylphosphono)butane]palladium chloride prepared according to Sugi, Y. et al., Chem. Lett., 1331 (1982) was added thereto at 0° C. Then, 3.2 ml of a 1M tetrahydrofuran solution of lithium triethylborohydride was added thereto dropwise, followed by stirring at –20° C. for 24 hours. After the reaction, a saturated ammonium chloride aqueous solution was added to the reaction mixture, and the mixture was extracted with ethyl acetate. The organic layer was washed with a saturated sodium chloride aqueous solution, dried over anhydrous magnesium, and concentrated. The concentrate was purified by silica gel chromatography (2% ethyl acetate in n-hexane) to give 0.15 g (41%) of 4,6-di-t-butyl-5-hydroxy-2-methyl-2-(4,8-dimethylnona-3(E),7-dienyl)-2,3-dihydrobenzothiophene as a colorless oil.

$^1$H NMR (270 MHz, CDCl$_3$)

δppm: 1.39(s,9H), 1.47(s,3H), 1.52(s,9H), 1.59(s,3H), 1.61(s,3H), 1.67(s,3H), 1.70–1.88(m,2H), 1.94–2.18(m,6H), 3.31(d,1H,J=15.2 Hz), 3.39(d,1H,J=15.2 Hz), 5.06–5.19(m, 2H), 5.10(s,1H), 6.97(s, 1H)

IR(cm$^{-1}$): 3644, 2960

Mass: 428(M$^+$)

Example 10

Synthesis of 4,6-Di-t-butyl-5-hydroxy-2-methyl-2-(4,8-dimethylnonyl)-2,3-dihydrobenzothiophene In 20 ml of a 9:1 mixture of ethyl acetate and acetic acid was dissolved 0.1 g of 4,6-di-t-butyl-5-hydroxy-2-methyl-2-(4,8-dimethylnona-3(E),7-dienyl)-2,3-dihydrobenzothiophene obtained in Example 9. To the solution was added 0.5 g of 10% palladium-on-carbon, followed by stirring for 24 hours under a hydrogen atmosphere. Palladium-on-carbon was removed by filtration, and the filtrate was concentrated. The concentrate was purified by silica gel chromatography (4% ethyl acetate in n-hexane) to give 0.09 g (91%) of 4,6-di-t-butyl-5-hydroxy-2-methyl-2-(4,8-dimethylnonyl)-2,3-dihydrobenzothiophene as a colorless oil.

$^1$H NMR (270 MHz, CDCl$_3$)

δppm: 0.86(dd,9H,J=6.6 Hz,J=3.0 Hz), 1.05–1.35(m, 12H), 1.39(s,9H), 1.45(s,3H), 1.52(s,9H), 1.56–1.83(m,2H), 3.30(d,1H,J=15.2 Hz), 3.36(d,1H,J=15.2 Hz), 5.10(s,1H), 6.97(s,1H)

IR(cm$^{-1}$): 3648, 2952

Mass: 432(M$^+$)

Example 11

Synthesis of 4,6-Di-t-butyl-5-hydroxy-2-methyl-2-(4,8,12-trimethytrideca-3(E), 7(E),11-trienyl)-2,3-dihydrobenzothiophene The title compound was obtained in the same manner as in Example 9.

$^1$H NMR (270 MHz, CDCl$_3$)

δppm: 1.39(s,9H), 1.47(s,3H), 1.52(s,9H), 1.59(s,6H), 1.61(s,3H), 1.68(s,3H), 1.71–1.88(m,2H), 1.90–2.19(m, 10H), 3.31(d,1H,J=15.2 Hz), 3.38(d,1H,J=15.2 Hz), 5.00–5.16(m,3H), 5.10(s,1H), 6.97(s,1H)

IR(cm$^{-1}$): 3644, 2960

Mass: 496(M$^+$)

Example 12

Synthesis of 4,6-Di-t-butyl-5-hydroxy-2-methyl-2-(4,8,12-trimethyltridecyl)-2,3-dihydrobenzothiophene The title compound was obtained in the same manner as in Example 10.

$^1$H NMR (270 MHz, CDCl$_3$)

δppm: 0.83–0.88(m,12H), 0.99–1.28(m,18H), 1.39(s, 9H), 1.45(s,3H), 1.52(s,9H), 1.55–1.75(m,3H), 3.30(d,1H, J=15.2 Hz), 3.36(d,1H,J=15.2 Hz), 5.10(s,1H), 6.97(s,1H)

IR(cm$^{-1}$): 3648, 2952

Mass: 502(M$^+$)

The following Test Examples 1 to 3 will prove the compounds of the invention excellent as an antioxidant.

[Test Case 1]

Amount of TBARS

Rabbit LDL was prepared in accordance with the method of Havel et al. [Havel, R. J. et al., J. Clin. Invest., 34, 1345 (1955)]. After adding 5 μM of $Cu^{2+}$, the mixture was warmed until a thiobarbituric acid reactive substance (TBARS) was produced. The test compounds were evaluated for their anti-oxidative action with the amount of TBARS being used as an index.

$$TBARS\ produced = \frac{TBARS\ produced\ when\ sample\ was\ added}{TBARS\ produced\ in\ solvent} \times 100(\%)$$

The results are shown in Table 1.

TABLE 1

| Compound | TBARS produced (%) | |
|---|---|---|
| | at $10^{-6}M$ of compound | at $10^{-5}M$ of compound |
| 1 | 89.6 | 4.3 |
| 2 | 31.7 | 3.5 |
| 3 | 16.9 | 3.1 |
| 4 | 92.7 | 37.6 |
| 5 | 9.8 | 2.8 |

[Test Case 2]

Effect Against Lipid Peroxidation by Autoxidation of Linoleic Acid

Using a cypridina luciferin analog (2-methyl-6-(p-methoxyphenyl)-3,7-dihydroimidazo[1,2-a]pyrazin-3-one: MCLA) as a sensitizer for lipid peroxyl radicals, the test compounds were evaluated for their inhibitory effect against the generation of lipid peroxyl radicals by autoxidation of linoleic acid. A n-butanol solution (0.5 ml) containing MCLA (0.2 μM) and linoleic acid (10 mM) was used in a chemiluminescence measuring vial and the intensity of chemiluminescence due to the autoxidation of linoleic acid was measured in a thermostatic bath at 37° C.

$$MCLA = \frac{Change\ in\ chemiluminescence\ intensity\ when\ sample\ was\ added}{Change\ in\ chemiluminescence\ intensity\ when\ solvent\ was\ added} \times 100(\%)$$

The results are shown in Table 2.

TABLE 2

| Compound | MCLA (%) | |
|---|---|---|
| | at $2 \times 10^{-5}M$ of compound | at $2 \times 10^{-4}M$ of compound |
| 1 | 7.2 | 0.9 |
| 2 | 26.8 | 1.1 |
| 3 | 9.4 | 0.9 |
| 4 | 73.3 | 19.7 |
| 5 | 17.7 | 0.7 |

[Test Case 3]

Effect Against Fluorescence Generation of Rabbit LDL by AAPH

Using 2,2'-azobis(2-aminodipropane)hydrochloride (AAHP) which was a radical initiator for a lipid peroxidation that was not mediated by active oxygen [see Sato, K. et al., Arch. Biochem. Biophys., 279, 402 (1990)], the test compounds were evaluated for their inhibitory effect against florescence generation in rabbit LDL. Rabbit LDL was prepared in accordance with the method of Havel [Havel, R. J. et al., J. Clin. Invest., 34, 1345 (1955)]; after addition of AAPH (2 mM), the mixture was warmed at 37° C. for 24 h and LDL fraction was separated by gel-permeation chromatography. The fluorescence intensity of LDL fraction was measured by fluorometry at an excitation wavelength of 360 nm and at an emission wavelength of 430 nm.

$$AAPH = \frac{Flourescence\ intensity\ of\ LDL\ fraction\ when\ sample\ was\ added}{Flourescence\ intensity\ of\ LDL\ fraction\ when\ solvent\ was\ added} \times 100(\%)$$

The results are shown in Table 3.

TABLE 3

| Compound | AAPH (%) at $10^{-4}M$ of compound |
|---|---|
| 1 | 29.0 |
| 2 | 11.9 |
| 3 | 13.1 |
| 4 | 70.5 |
| 5 | 15.3 |

The results of Test Cases 1–3 obviously show that the tested compounds of the invention had an excellent anti-oxidative activity. The active oxygen induced by $Cu^{2+}$ in the TBARS experimental model in Test Case 1 is believed to be a direct radical initiator, so even a water-soluble active oxygen scavenger will be effective in that model. It should, however, be stressed that the tested compounds of the invention also proved to be effective in the AAPH using experimental model in Test Case 3 and, hence, it became clear that those compounds also suppressed the chain reaction for lipid peroxidation due to carbon-centered radicals which could not be inhibited by water-soluble active oxygen scavengers. This fact suggests that the compounds of the invention show effective anti-oxidative actions in LDL oxidation or lipid peroxidation.

Industrial Applicability

The compounds represented by formula (I) exhibit an inhibitory action on the oxidative modification of LDL and are useful as therapeutics of arteriosclerosis. Further, the compounds represented by formula (II) are useful as intermediates for synthesis of the compounds of formula (I).

We claim:

1. A compound represented by formula (I'):

(I')

wherein $R_1$ represents a hydrogen atom, a lower alkyl group or an acyl group; $R_2$ and $R_3$, which may be the same or different, each represents a hydrogen atom, an optionally substituted alkyl group, or an optionally substituted alkenyl group; $R_4$ represents a hydrogen atom, an optionally substituted alkyl group, or an optionally substituted alkenyl group; and n represents an integer of 0 to 2, or a pharmaceutically acceptable salt thereof.

2. A compound represented by formula (I) according to claim 1 or a pharmaceutically acceptable salt thereof, wherein $R_1$, $R_2$, $R_3$, and $R_4$ are as defined above; and n represents 0.

3. A compound represented by formula (I) according to claim 1 or a pharmaceutically acceptable salt thereof, wherein $R_1$, $R_2$, $R_3$, and $R_4$ are as defined above; and n represents 2.

4. A compound represented by formula (II):

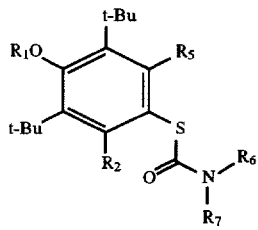

wherein $R_1$ represents a hydrogen atom, a lower alkyl group or an acyl group; $R_2$ represents a hydrogen atom, an optionally substituted alkyl group, or an optionally substituted alkenyl group; $R_5$ represents a group of formula (III):

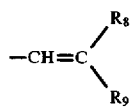

wherein $R_8$ and $R_9$, which may be the same or different, each represents a hydrogen atom, an optionally substituted alkyl group or an optionally substituted alkenyl group, a group of formula (IV):

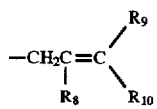

wherein $R_8$, $R_9$, and $R_{10}$, which may be the same or different, each represents a hydrogen atom, an optionally substituted alkyl group or an optionally substituted alkenyl group, or a group of formula (V):

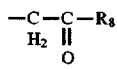

wherein $R_8$ represents a hydrogen atom, an optionally substituted alkyl group, or an optionally substituted alkenyl group, and $R_6$ and $R_7$, which may be the same or different, each represents a lower alkyl group, or a pharmaceutically acceptable salt thereof.

5. A compound represented by formula (II) according to claim 4 or a pharmaceutically acceptable salt thereof, wherein $R_1$ represents a hydrogen atom, a lower alkyl group or an acyl group; $R_2$ represents a hydrogen atom, an optionally substituted alkyl group, or an optionally substituted alkenyl group; $R_5$ represents a group of formula (III):

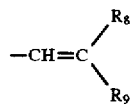

wherein $R_8$ and $R_9$, which may be the same or different, each represents a hydrogen atom, an optionally substituted alkyl group or an optionally substituted alkenyl group, and $R_6$ and $R_7$, which may be the same or different, each represents a lower alkyl group.

6. A compound represented by formula (II) according to claim 4 or a pharmaceutically acceptable salt thereof, wherein $R_1$ represents a hydrogen atom, a lower alkyl group or an acyl group; $R_2$ represents a hydrogen atom, an optionally substituted alkyl group, or an optionally substituted alkenyl group; $R_5$ represents a group of formula (IV):

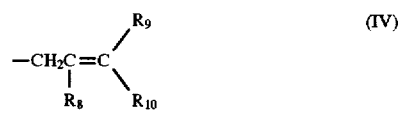

wherein $R_8$, $R_9$, and $R_{10}$, which may be the same or different, each represents a hydrogen atom, an optionally substituted alkyl group or an optionally substituted alkenyl group, and $R_6$ and $R_7$, which may be the same or different, each represents a lower-alkyl group.

7. A compound represented by formula (II) according to claim 4 or a pharmaceutically acceptable salt thereof, wherein $R_1$ represents a hydrogen atom, a lower alkyl group or an acyl group; $R_2$ represents a hydrogen atom, an optionally substituted alkyl group, or an optionally substituted alkenyl group; $R_5$ represents a group of formula (V):

wherein $R_8$ represents a hydrogen atom, an optionally substituted alkyl group, or an optionally substituted alkenyl group, and $R_6$ and $R_7$, which may be the same or different, each represents a lower alkyl group.

8. A compound represented by formula (I')

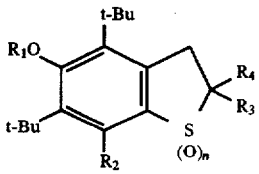

wherein $R_1$ represents a hydrogen atom, a lower alkyl group or an acyl group; $R_2$ represents a hydrogen atom, an optionally substituted alkyl group, or an optionally substituted alkenyl group; $R_3$ and $R_4$, which may be the same or different, each represents an optionally substituted alkyl group, or an optionally substituted alkenyl group, and $R_3$ and $R_4$ are taken together to form a 5- to 8-membered spiro ring which may contain a hetero atom selected from oxygen, sulfur or nitrogen; and n represents an integer of 0 to 2, or a pharmaceutically acceptable salt thereof.

9. In a pharmaceutical composition comprising a pharmaceutical carrier and an active compound for the treatment of arteriosclerosis, the improvement wherein said active compound is a compound represented by formula (I'):

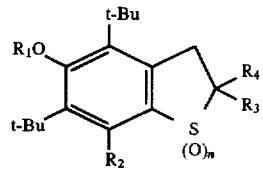

wherein $R_1$ represents a hydrogen atom, a lower alkyl group or an acyl group; $R_2$ and $R_3$, which may be the same or different, each represents a hydrogen atom, an optionally substituted alkyl group, or an optionally substituted alkenyl group; R₄ represents a hydrogen atom, an optionally substituted alkyl group, or an optionally substituted alkenyl group; and n represents an integer of 0 to 2, or a pharmaceutically acceptable salt thereof.

10. The pharmaceutical composition according to claim 9, wherein R₁, R₂, R₃, and R₄ are defined above; and n represents 0.

11. A composition comprising an active compound dissolved in a lipid, said active compound comprising a compound represented by formula (I):

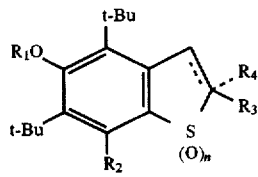

wherein R₁ represents a hydrogen atom, a lower alkyl group or an acyl group; R₂ and R₃, which may be the same or different, each represents a hydrogen atom, an optionally substituted alkyl group, or an optionally substituted alkenyl group; R₄ represents a hydrogen atom, an optionally substituted alkyl group, or an optionally substituted alkenyl group, or R₄ forms a double bond between the carbon atom to which R₃ is bonded and the adjacent carbon atom to form a benzothiophene skeleton; and n represents an integer of 0 to 2, or a pharmaceutically acceptable salt thereof.

12. The composition according to claim 11, wherein R₁, R₂, and R₃ are defined above. R₄ represents a hydrogen atom, an optionally substituted alkyl group, or an optionally substituted alkenyl group, or R₄ forms a double bond between the carbon atom to which R3 is bonded and the adjacent carbon atom to form a benzothiophene skeleton; and n represents 0.

13. A method for the treatment of arteriosclerosis comprising administering to a patient in need of said therapy an amount sufficient of an active compound to exhibit an inhibitory action on the oxidative modification of LDL, said active compound being represented by formula (I):

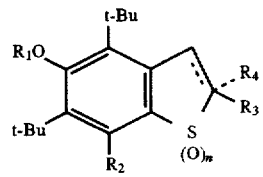

wherein R₁ represents a hydrogen atom, a lower alkyl group or an acyl group; R₂ and R₃, which may be the same or different, each represents a hydrogen atom, an optionally substituted alkyl group, or an optionally substituted alkenyl group; R₄ represents a hydrogen atom, an optionally substituted alkyl group, or an optionally substituted alkenyl group, or R₄ forms a double bond between the carbon atom to which R₃ is bonded and the adjacent carbon atom to form a benzothiophene skeleton; and n represents an integer of 0 to 2, or a pharmaceutically acceptable salt thereof.

14. A method for inhibiting oxidative modification of LDL in a patient in need of said therapy, comprising administering to said patient an amount effective of an active compound to inhibit the oxidative modification of LDL, said active compound being represented by formula (I):

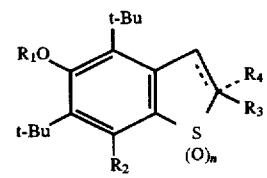

wherein R₁ represents a hydrogen atom, a lower alkyl group or an acyl group; R₂ and R₃, which may be the same or different, each represents a hydrogen atom, an optionally substituted alkyl group, or an optionally substituted alkenyl group; R₄ represents a hydrogen atom, an optionally substituted alkyl group, or an optionally substituted alkenyl group, or R₄ forms a double bond between the carbon atom to which R₃ is bonded and the adjacent carbon atom to form a benzothiophene skeleton; and n represents an integer of 0 to 2, or a pharmaceutically acceptable salt thereof.

* * * * *

UNITED STATES PATENT AND TRADEMARK OFFICE
CERTIFICATE OF CORRECTION

PATENT NO. : 5,789,436
DATED : Aug. 4, 1998
INVENTOR(S) : Kato et al.

It is certified that error appears in the above-identified patent and that said Letters Patent is hereby corrected as shown below:

Cover page, title of invention, line [54], delete "5-Hydroxy-"; and add --Derivatives-- at the end of the title; and Column 1, line 4, delete "5-Hydroxy-"; and line 5, after "Thiophene" add --Derivatives--.

Signed and Sealed this

First Day of December, 1998

Attest:

BRUCE LEHMAN

Attesting Officer

Commissioner of Patents and Trademarks